(12) United States Patent
Imamura et al.

(10) Patent No.: US 6,660,516 B1
(45) Date of Patent: Dec. 9, 2003

(54) METHOD FOR CULTURING A MICROORGANISM AND PROMOTING MICROBIAL GROWTH AND METABOLISM

(75) Inventors: Takeshi Imamura, Chigasaki (JP); Yasutsugu Yamada, Yokohama (JP); Tetsuya Yano, Atsugi (JP); Akira Kuriyama, Atsugi (JP); Shinya Kozaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/025,424

(22) Filed: Feb. 18, 1998

(30) Foreign Application Priority Data

Feb. 18, 1997 (JP) .............................................. 9-033868
Feb. 18, 1997 (JP) .............................................. 9-033870

(51) Int. Cl.[7] .............................. B09B 3/00; C12N 1/00; C12N 1/12; C12N 1/20

(52) U.S. Cl. ................. 435/252.8; 435/243; 435/252.1; 435/252.3; 435/253.6; 435/262.5; 435/822; 435/849

(58) Field of Search .............................. 435/243, 252.1, 435/262.5, 822, 210, 600, 610, 252.3, 252.8, 253.6, 849

(56) References Cited

U.S. PATENT DOCUMENTS

| | | | |
|---|---|---|---|
| 4,877,736 A | 10/1989 | Fliermans | 435/183 |
| 4,925,802 A | 5/1990 | Nelson et al. | 435/262 |

FOREIGN PATENT DOCUMENTS

| | | |
|---|---|---|
| JP | 02-92274 | 4/1990 |
| JP | 06-62831 | 3/1994 |
| JP | 06-70753 | 3/1994 |
| JP | 06-210297 | 8/1994 |
| JP | 07-123976 | 5/1995 |
| JP | 07-236895 | 9/1995 |
| JP | 08-70881 | 3/1996 |
| JP | 08-117777 | 5/1996 |

OTHER PUBLICATIONS

Database WP1, Section Ch, Wk. 9017, Derwent, AN–130969, XP 2105439 for SU1 493667.
Database WP1, Secrtion Ch, Wk. 9612, Derwent, AN96–111017, XP002105440 for JP 08–10789.
Patent Abst. of Japan, 99, 004, 4/99 for JP11–10123.
Patent Abst. of Japan, 99, 002, 2/99 for JP10–295366.
Patent Abst. of Japan, 96, 008, 8/96, for JP08–89271.
Patent Abst. of Japan, 96, 002, 2/96 for JP 07–284792.
Nelson, et al., "Aerobic Metabolism of Trichloroethylene by a Bacterial Isolate", Appl. & Environ. Microb., vol. 52, No. 2, Aug. 1986, pp. 383–384.
J. Japan Sewage Works Assn., vol. 24, No. 273, 1987, pp. 27–33.

Nelson, et al., "Biodegradation of Trichloroethylene and Involvement of an Aromatic Biodegradative Pathway", Appl. & Environ. Microb., vol. 53, No. 5, May 1987, pp. 949–954.
Little, et al., "Trichloroethylene Biodegradation by a methane–Oxidizing Bacterium", Appl. & Environ. Microb., vol. 54, No. 4, Apr. 1988, pp. 951–956.
Wackett, et al., "Degradation of Trichloroethylene by Toluene Dioxygenase in Whole–Cell Studies with *Pseudomonas putida* F1", Appl. & Environ. Microb., vol. 54, No. 7, Jul. 1988, pp. 1703–1708.
Vandenbergh, et al., "Metabolism of Volatile Chlorinated Aliphatic Hydrocarbons by *Pseudomonas fluorescens*", App. & Environ. Microb., vol. 54, No. 10, Oct. 1988, pp. 2578–2579.
Winter, et al., "Efficient Degradation of Trichloroethylene by a Recombinant *Escherichia Coli*", Bio/Technology, vol. 7, Mar. 1989, pp. 282–285.
Int. J. of Systematic Bacteriology, vol. 39, No. 3, Jul. 1989, pp. 369–371.
Uchiyama, et al., "Aerobic Degradation of Trichloroethylene by a new Type II Methane–Utilizing Bacterium, Strain M", Agric. Biol. Chem., vol. 53, No. 11, 1989, pp. 2903–2907.
Wackett, et al., "Survey of Microbial Oxygenases: Trichloroethylene Degradation by Propane–Oxidizing Bacteria", Appl. & Environ. Microb., vol. 55, No. 11, Nov. 1989, pp. 2960–2964.

(List continued on next page.)

*Primary Examiner*—David M. Naff
*Assistant Examiner*—Deborah K. Ware
(74) *Attorney, Agent, or Firm*—Fitzpatrick, Cella, Harper & Scinto

(57) ABSTRACT

A method is provided for culturing a microorganism in a culture medium containing a carbon source and an electrolyzed water containing not more than 0.4 ppm chlorine produced during electrolyzing water containing an electrolyte in an electrolytic cell. The culture medium may also contain a carbon source and an acidic water having a pH value of 1–4 and a redox potential from 800 mV to 1500 mV. The acidic water is obtained by electrolysis of water in an electrolytic cell. Further, the culture medium may contain a carbon source and an alkaline water having a pH value of 10–13 and a redox potential from –1000 mV to 800 mV. The alkaline water is obtained by electrolysis of water in an electrolytic cell. The redox potential for the alkaline water is determined by the use of a platinum electrode as a working electrode and a silver-silver chloride electrode as a reference electrode. The microorganism may be selected from *Escherichia coli*, strain J1, strain JM2N, or an artificial recombinant. The microorganism can decompose a pollutant, such as phenol, toluene, cresol, trichlorethylene and dichloroethylene.

32 Claims, 11 Drawing Sheets

OTHER PUBLICATIONS

Tsien, et al., "Biodegradation of Trichloroethylene by *Methylosinus trichosporium* OB3b", Appl. & Environ. Microbiol., vol. 55, No. 12, Dec. 1989, pp. 3155–3161.

Harker, et al., "Trichloroethylene Degradation by Two Independent Aromatic–Degrading Pathways in *Alcaligenes eutrophus* JMP134", Appl. & Environ. Microbiol., vol. 56, No. 4, Apr. 1990, pp. 1179–1181.

Vannelli, et al., "Degradation of Halogenated Aliphatic Compounds by the Ammonia–Oxidizing Bacterium *Nitrosomonas europaea*", Appl. & Environ. Microbiol., vol. 56, No. 4, Apr. 1990, pp. 1169–1171.

Folsom, et al., "Phenol and Trichloroethylene Degradation by *Pseudomonas cepacia* G4: Kinetics and Interactions between Substrates", Appl. & Environ. Microbiol., vol. 56, No. 5, May 1990, pp. 1279–1285.

Henry, et al., "Influence of Endogenous and Exogenous Electron Donors and Trichloroethylene Oxidation Toxicity on Trichloroethylene Oxidation by Methanotrophic Cultures from a Groundwater Aquifer", Appl. & Environ. Microbiol., vol. 57, No. 1, Jan. 1991, pp. 236–244.

Eng, et al., "Methanol Suppression of Trichloroethylene Degradation by *Methylosinus trichosporium* (OB3b) and Methane–Oxidizing Mixed Cultures", Appl. Biochem & Biotech., vol. 28/29, 1991, pp. 887–899.

Shields, et al., "Mutants of *Pseudomonas cepacia* G4 Defective in Catabolism of Aromatic Compounds and Trichloroethylene", Appl. & Environ. Microbiol., vol. 57, No. 7, Jul. 1991, pp. 1935–1941.

Beam, et al., "Microbial Degradation of Cycloparaffinic Hydrocarbons via Co–metabolism and Commensatism", J. Gen. Microbiol., vol. 82, (1974), pp. 163–169.

Ewers, et al., "Selection of trichloroethene (TCE) degrading bacteria that resist inactivation by TCE", Arch. Microbiol., vol. 154, 1990, pp. 410–413.

METHOD FOR CULTURING A MICROORGANISM AND PROMOTING MICROBIAL GROWTH AND METABOLISM

BACKGROUND OF THE INVENTION

1. Field of the Invention

This invention relates to a method for culturing a microorganism, a method for synthesizing an organic compound utilizing a microorganism, a method for maintaining the microbial decomposing ability of a pollutant, a method for decomposing a pollutant utilizing a microorganism, and a method for remedying an environment utilizing a microorganism.

2. Related Background Art

In recent years, utilization of microorganisms in production of useful substances or in degradation of harmful substances has been actively studied, with the development of the applied microbial engineering.

At the beginning, the microbial technology was mainly applied to the synthesis of medicines and hormones which are difficult to be chemically synthesized and of high value added, or to the treatment of sewage or waste water of which amount to be treated makes physical or chemical treatment too expensive.

Now, various technologies including genetic engineering have been greatly developed, which enables production or decomposition of various substances and variegates the field of the microorganism utilization.

For example, in the field of the environment purification by means of microbial decomposition, attention has been attracted to the remediation of the environment polluted with organic chlorine compounds which are harmful to organisms and difficult to degrade.

For example, the soil in the manufacturing area of paper and pulp industry and semiconductor industry in as abroad is considered to be contaminated with chlorinated organic compounds such as tetrachloroethylene (PCE), trichloroethylene (TCE), dichloroethylene (DCE) and the like. Actually there have been many reports on detection of such chlorinated organic compounds through environmental surveys.

It is supposed that chlorinated organic compounds remaining in soil dissolves in groundwater via rainwater etc. thus spread over the area. There is a strong suspicion that these compounds are carcinogens, and further, these are quite stable in the environment; therefore contamination of groundwater, which is used as a source of drinking water, is a serious social problem.

The examples of strains capable of degrading TCE are given as follows:

*Welchia alkenophila* sero 5; ATCC 53570 (U.S. Pat. No. 4,877,736)
*Welchia alkenophila* sero 33; ATCC 53571 (U.S. Pat. No. 4,877,736)
*Methylocystis* sp. strain M (Agric. Biol. Chem., 53, 2903 (1989), Biosci. Biotech. Biochem., 56, 486 (1992), ibid. 56, 736 (1992)
*Methylosinus trichosporium* OB3b (Am. Chem. Soc. Natl. Meet. Dev. Environ. Microbiol., 55, 3155 (1989), Appl. Environ. Microbiol., 55, 3155 (1989), Appl. Biochem. Biotechnol., 28, 887 (1991), Japanese Laid-Open Patent Application No. (JP-A)-2-92,274, JP-A-3-392,970
*Methylomonas* sp. MM2 (Appl. Environ. Microbiol., 57, 236 (1991)
*Alcaligenes denitrificans* sp. xylosoxidans JE 75 (Arch. microbiol., 154, 410 (1990)
*Alcaligenes eutrophus* JMP 134 (Appl. Environ. Microbiol., 56, 1179 (1990)
*Alicaligenes eutrophus* FERM P-13761 (JP-A-7-123,976)
*Pseudomonas aeruginosa* J1104 (JP-A-7-236,895)
*Mycobacterium vaccae* JOB5; ATCC 29678 (J. Gen. Microbiol., 82, 163 (1974), Appl. Environ. Microbiol., 53, 2960 (1989)
*Pseudombnas putida* BH (Journal of Japan Sewage Work Association 24., 27 (1987)
*Pseudomonas* sp. G4; ATCC 53617 (Appl. Environ. Microbiol., 52, 383 (1986), ibid. 53, 9494 (1987), ibid. 54, 951 (1988), ibid. 56, 1279 (1990), ibid. 57, 1935 (1991), U.S. Pat. No. 4,925,802
*Pseudomonas mendocina* KR-1 (Bio/Technol., 7, 282 (1989))
*Pseudomonas putida* F1 (Appl. Environ. Microbiol., 54, 1703 (1988), ibid. 54, 2578 (1988))
*Pseudomonas fluorescens* PFL 12 (Appl. Environ. Microbiol., 54, 2578 (1988))
*Pseudomonas putida* KWI-9 (JP-A-6-70,753)
*Pseudomonas cepacia* KK 01 (JP-A-6-227,769)
*Nitrosomonas europaea* (Appl. Environ. Microbiol., 56, 1169 (1990))
*Lactobacillus vaginalis* sop. nov; ATCC 49540 (Int. J. syst. Bacteriol., 39, 368 (1989)
*Nocardia corallina* B-276; FERM BP-5124, ATCC 31338 (JP-A-8-70,881)

In the field of microbial production, the production of pharmacologically active substances and enzymes has been drawing attention.

In the above mentioned fields of microbiological technology, high cost is a common obstacle. To overcome this problem, for example, in the field of the microbial substance production, it has been proposed a method for economic operation of a reactor by operating the reactor measuring the cell concentration and redox potential in the reactor to introduce the optimal amount of substrate and air according to the predetermined optimal relationship between the cell mass, substrate concentration and aeration (JP-A-04-231,601 and JP-A-06-210,297). JP-A-06-062,831 teaches to design the shape of a reactor for efficient growth of the producing microorganism and recovery of cells and the synthesized product. Also in the field of the microbial degradation of organic compounds and environment remediation, various technologies have been developed to improve the degradation efficiency of the organic compound. JP-A-8-117,777, for example, discloses a method for improving the mixing efficiency of the microbe-holding carrier in a liquid-flow type biochemical reaction device.

SUMMARY OF THE INVENTION

The present inventors have made various studies to improve the efficiency in the microbial manufacturing, and in microbial decomposition of organic compounds, and found that the use of electrolyzed water is highly effective in improving the efficiency of the microbial proliferation, which is extremely advantageous for efficient microbial production of a substance, and in improving the efficiency of the microbial decomposition of organic compounds. Specifically, it has been found that when a microorganism is grown in a culture medium containing electrolytic water, the growth rate and the maximum cell density are both greater than those in an ordinary culture medium. It has been also found that when an organic compound is degraded by a microorganism in the presence of electrolytic water, the organic compound is decomposed in a shorter period of time than in a control medium.

The present invention has been made on the novel findings mentioned above. An object of this invention is to provide a method for cultivating a microorganism more efficiently.

Another object of this invention is to provide a method for producing an organic compound by using a microorganism more efficiently.

Another object of this invention is to provide a method for degrading a pollutant more efficiently by using a microorganism which is capable of decomposing the pollutant.

Another object of this invention is to provide a method for decomposing an organic compound more efficiently by the use of a microorganism.

Yet another object of this invention is to provide a more efficient method for remedying an environment utilizing microorganisms.

To accomplish the objects mentioned above, one embodiment of the present invention provides a method for culturing a microorganism which comprises a step of culturing the microorganism in a culture medium containing a carbon source being metabolizable by the microorganism and an electrolyzed water obtained by electrolysis of water in an electrolytic cell.

According to the other embodiment of the present invention, there provided is a method for culturing a microorganism comprising a step of culturing the microorganism in a culture medium containing a carbon source being metabolizable by the microorganism and an acidic water having a pH value of 1–4 and redox potential of 800 mV–1500 mV.

According to the other embodiment of the present invention, there provided is a method for culturing a microorganism comprising a step of culturing the microorganism in a culture medium containing a carbon source being metabolizable by the microorganism and an alkaline water having a pH value of 10–13 and a redox potential of –1000 mV–800 mV determined by using a platinum electrode as a working electrode and a silver-silver chloride electrode as a reference electrode.

By means of the constitution of the present invention, the growth rate and the maximum cell density in the culture medium are increased.

To accomplish the objects mentioned above, one embodiment of the present invention provides a method for producing an organic compound using a microorganism which comprises a step of reacting a first compound with a microorganism capable of producing a second organic compound from the first organic compound in the presence of an electrolyzed water obtained by electrolysis of water in an electrolytic cell.

According to the other embodiment of the present invention, there provided is a method for producing an organic compound using a microorganism which comprises a step of reacting a first compound with a microorganism capable of producing a second organic compound from the first organic compound in the presence of an acidic water having a pH value of 1–4 and an oxidation-reduction potential of 800 mV–1500 mV.

According to the other embodiment of the present invention, there provided is a method for producing an organic compound using a microorganism which comprises a step of reacting a first compound with a microorganism capable of producing a second organic compound from the first organic compound in the presence of an alkaline water having a pH value of 10–13 and an oxidation-reduction potential of –1000 mV–800 mV determined by using a platinum electrode as a working electrode and a silver—silver chloride electrode as a reference electrode.

To accomplish the objects mentioned above, one embodiment of the present invention provides a method, for producing an organic compound using a microorganism which comprises cultivating a microorganism capable of producing from a first organic compound a second organic compound in a culture medium containing a carbon source and an electrolyzed water obtained by electrolysis of water in an electrolytic cell; isolating the grown microorganism from the culture medium; and reacting the microorganism with the first compound to produce the second organic compound.

By means of the constitution described above, the productivity of the microbial production of a substance can be improved.

To accomplish the objects mentioned above, one embodiment of the present invention provides a method for maintaining an ability of a microorganism to decompose a pollutant which comprises a step of culturing a microorganism expressing a pollutant-decomposing activity in a culture medium containing an electrolyzed water obtained by electrolysis of water in an electrolytic cell.

To achieve the above objects, one embodiment of the present invention provides a method for degrading a pollutant which comprises a step of contacting a microorganism having a pollutant-decomposing ability with a pollutant in a presence of an electrolyzed water obtained by electrolysis of water in an electrolytic cell.

According to the other embodiment of the present invention, there provided is a method for degrading a pollutant which comprises a step of contacting a microorganism having a pollutant-decomposing ability with a pollutant in the presence of an acidic water having a pH value of 1–4 and a redox potential of 800 mV–1500 mV.

According to the other embodiment of the present invention, there provided is a method for degrading a pollutant which comprises a step of contacting a microorganism having a pollutant-decomposing ability with a pollutant in the presence of an alkaline water having a pH value of 10–13 and a redox potential of –1000 mV–800 mV determined by using a platinum electrode as a working electrode and a silver—silver chloride electrode as a reference electrode.

To accomplish the objects mentioned above, one embodiment of the present invention provides a method for remedying an environment which comprises a step of decomposing a pollutant contained in the environment by contacting the pollutant with a microorganism capable of decomposing the pollutant in the presence of a water containing an electrolyzed water obtained by electrolysis of water in an electrolytic cell.

According to the other embodiment of the present invention, there provided is a method for remedying an environment which comprises a step of decomposing a pollutant contained in the environment by contacting the pollutant with a microorganism capable of decomposing the pollutant in the presence of an acidic water having a pH value of 1–4 and a redox potential of 800 mV–1500 mV.

According to the other embodiment of the invention, there provided is a method for remedying an environment which comprises a step of decomposing a pollutant contained in the environment by contacting the pollutant with a microorganism capable of decomposing the pollutant in the presence of an alkaline water having a pH value of 10–13 and a redox potential of −1000 mV–800 mV determined by using a platinum electrode as a working electrode and a silver—silver chloride electrode as a reference electrode.

By means of the constitution described above, the efficiency of the decomposition of the pollutant and the purification of the environment is much improved.

Further, the advantage of the present invention is that the microorganism can function effectively even under conditions detrimental to the activity of the microorganism, e.g. the temperature as low as 4° C. or a presence of an organic solvent in a concentration exceeding 1% in the culture medium which are generally harsh conditions for the viability and growth of microorganisms.

DETAILED DESCRIPTION OF THE PREFERRED EMBODIMENTS

[Microbial Culture of Microorganism with the Electrolyzed Water]

One embodiment of the method for the culture of a microorganism is characterized in that in one step the microorganism is cultured in a culture medium containing a carbon source being metabolizable by the microorganism and an electrolyzed water obtained by electrolysis of water in an electrolytic cell.

The present invention has been made based on the novel findings of the inventors' that the electrolyzed water, obtainable by electrolysis of water in an electrolytic cell, can increase the growth rate of microorganisms and the maximum cell number in the culture, and when the microorganism possesses the ability to decompose a pollutant, the electrolyzed water makes the microorganism maintain this ability of decomposition for a long time.

The method for producing an organic compound using a microorganism of the present invention which comprises a step of reacting a first compound with a microorganism capable of producing a second organic compound from the first organic compound in the presence of an electrolyzed water obtained by electrolysis of water in an electrolytic cell. This invention has been made based on the novel findings of the inventors' that the electrolyzed water obtainable by electrolysis of water in an electrolytic cell improves the substance-converting ability of a microorganism.

Figure 1:
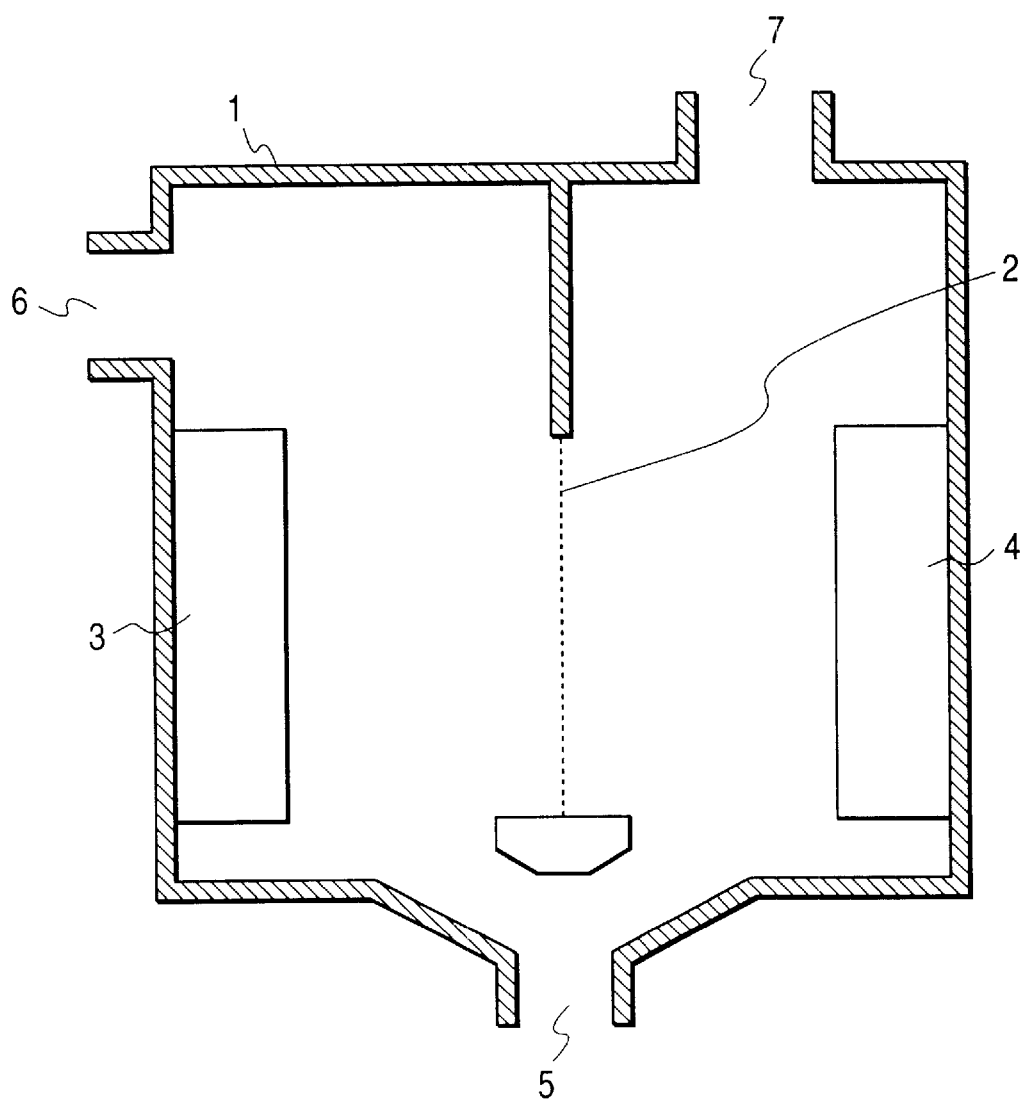
FIG. 1 is a schematic cross section of a device for the production of the electrolyzed water.

The electrolyzed water can be produced, for example, according to the following procedure. FIG. 1 is a schematic diagram of a device for the production of the electrolyzed water. Devices of similar constitution are disclosed in JP-A-64-11,693, JP-A-3-39,293, and JP-A-3-238,084. With reference to FIG. 1, 1 is an electrolytic cell, 2 is a diaphragm, 3 is an anode, 4 is a cathode, 5 is a water inlet, 6 is an outlet for the electrolyzed water formed on the anode side, and 7 is an outlet for the electrolyzed water formed on the cathode side. When water is supplied through the water inlet 5 to the anode 3 side and the cathode 4 side of the cell 1 and then a DC voltage is applied between the electrodes to effect electrolysis of the water, the water containing cations and exhibiting an alkalinity (hereinafter referred to as "alkaline water") gathers on the cathode 4 side and the water containing anions and exhibiting acidity (hereinafter referred to as "acidic water") gathers on the anode 3 side. The water to be supplied through the water inlet 5 to the cell 1 (hereinafter referred to as "raw water") may be processed water such as deionized water and purified water, and tap water and groundwater can also be used.

Acidic water or alkaline water obtained as described above is suitable to use as the electrolyzed water in the embodiments mentioned above.

Acidic water preferably has a hydrogen ion concentration (pH) value in a range of 1–4 and a redox potential, determined by using a platinum electrode as a working electrode and a silver—silver chloride electrode as a reference electrode, in the range of 800–1500 mV, more preferably, pH of not more than 2.8 and a redox potential of not less than 800 mV, and furthermore preferably pH of not more than 2.8 and a redox potential of not less than 1100 mV, from the viewpoint of the microbial growth and the maximum cell number in the culture medium.

Alkaline water preferably has a pH value in the range of 10–13 and a redox potential, determined by using a platinum electrode as a working electrode and a silver—silver chloride electrode as a reference electrode, in the range of −1000–800 mV, more preferably, pH of not less than 10.5 and a redox potential of not more than −600 mV, and further more preferably pH of not less than 11 and a redox potential of not more than −800 mV, from the viewpoint of the microbial growth and the maximum cell number in the culture medium.

The acidic water or the alkaline water of the quality mentioned above can be obtained by electrolyzing a raw water containing an electrolyte (such as, for example, sodium chloride or potassium chloride) in a cell provided with a pair of electrodes, and by collecting water near the electrodes. The concentration of the electrolyte, e.g. sodium chloride, dissolved in the raw water prior to the electrolysis is preferably in the range of 20 mg/l–2000 mg/l. It is desirable to set the electrolytic current in a range of 2 A–20 A. When as diaphragm 2 is provided an ion-exchange membrane which prevents the movement of electrolyte solutions around the electrodes to the opposite sides, but allows irreversible migration of the cations such as $Na^+$, $Ca^{2+}$, $Mg^{2+}$, $K^+$ existing around the anode to the cathode side, and of anions such as $Cl^-$, $SO_4^{2-}$, $HCO_3^-$ existing around the cathode to the anode side, the acidic water formed near the anode and the alkaline water formed near the cathode would not mix with each other and the acidic water or the alkaline water of the desired quality can be efficiently obtained. As a device for obtaining such a functional water as mentioned above, a commercially available strongly acidic electrolyzed water maker (a product of Asahi Glass Engineering K.K. under a trade name of "Oasis Biohalf") can be utilized. Besides sodium chloride, other salts such as potassium chloride, calcium chloride, and calcium carbonate can be used as the electrolyte.

When a chloride such as sodium chloride is used as the electrolyte, it is preferred to dechlorinate the acidic water prior to the contact with the microorganism because such an acidic water contains dissolved chlorine. As an example of the dechlorinating treatment, the acidic water obtained with the electrolyzing device mentioned above is stirred with UV irradiation. In view of the acceleration of the microbial growth rate or the biosynthesis efficiency of organic compounds, it is desirable to reduce the chlorine concentration (determined with a CL meter, a product of Cosmos Denki K.K. under product code of "EM-240W"), to less than 0.4 ppm, preferably less than 0.3 ppm.

[Culture Method]

The culture method according to one embodiment of the present invention, is characterized in that the microorganism is cultured in a culture medium containing the electrolyzed water and a carbon source being metabolizable by the microorganism. The content of the electrolyzed water in the culture medium is not less than 10 wt %, preferably 60 wt % or more, based on the total weight of the culture medium. A culture medium containing the electrolyzed water can be prepared by dissolving necessary salts in the electrolyzed water. The examples of the culture medium include M9 medium containing salts in a composition shown in Table 1 and MSB medium containing salts in a composition shown in Table 2. Any culture method can be used as long as the microorganism can grow in the culture medium containing the electrolyzed water. As examples of the methods, batch, semicontinuous, and continuous methods may be used. Further, a closed system or an open system may be suitably selected for the culture.

TABLE 1

Composition of M9 medium

| | |
|---|---|
| $Na_2HPO_4$: | 6.2 g |
| $KH_2PO_4$: | 3 g |
| NaCl: | 0.5 g |
| $NH_4Cl$: | 1 g |

TABLE 2

Composition of MSB medium

| | |
|---|---|
| $Na_2HPO_4$ + $KH_2PO_4$ (1 M, pH 6.8) | 40 ml |
| Hunter's vitamin-free mineral base*1 | 20 ml |
| $(NH_4)_2SO_4$ | 1 g |

TABLE 2-continued

Composition of MSB medium

| | |
|---|---|
| Water | 840 ml |

*1: Hunter's vitamin-free mineral base:

| | |
|---|---|
| Nitrilotriacetic acid | 10.0 g |
| $MgSO_4$ | 14.45 g |
| $CaCl_2.2H_2O$ | 3.335 g |
| $(NH_4)_6MO_7O_{24}.4H_2O$ | 9.25 mg |
| $FeSO_4.7H_2O$ | 99 mg |
| Metals "44"*2 | 50 ml |
| Distilled water | |
| Added to total volume of 1000 ml | |

*2: Metals: "44":

| | |
|---|---|
| Ethylene diamine tetraacetic acid | 250.0 mg |
| $ZnSO_4.7H_2O$ | 1095.0 mg |
| | (250 mg Zn) |
| $FeSO_4.7H_2O$ | 500.0 mg |
| | (100 mg Fe) |
| $MnSO_4.H_2O$ | 154.0 mg |
| | (50 mg Mn) |
| $CuSO_4.5H_2O$ | 39.2 mg |
| | (10 mg Cu) |
| $Co(NO_3)_2.6H_2O$ | 24.8 mg |
| | (5 mg Co) |
| $Na_2B_4O_7.10H_2O$ | 17.7 mg |
| | (2 mg B) |

Several drops of sulfuric acid to prevent precipitation
Distilled water 100 ml

[Microorganism]

The only requirement for the microorganism to be used for the culture is that it can grow in a culture medium containing the electrolyzed water. Examples of the microorganisms include microorganisms isolated from nature, microorganisms isolated from nature and mutagenized, and recombinant microorganisms containing a gene derived from a microorganism isolated from nature (e.g. *Escherichia coli*, JM109). As examples of the microorganism isolated from nature, there are strain JI (FERM BP-5102) and *Burkholderia cepacia* KK01 (FERM BP-4235). As examples of the microorganism isolated from nature and mutagenized, there is strain M1 (FERM BP-5352) and strain JM2N (FERM BP-5961).

[Culture Conditions]

It is desirable to carry out the cultivation under the optimum conditions for the microorganism to be used. These conditions may be determined suitably according to the microorganism to be used. A certain microorganism may be cultured under an aerobic conditions in a liquid culture or a solid culture. Further, the culture temperature is usually the optimum temperature for the microorganism in use. The microorganism may be optionally immobilized in advance on a carrier. Various methods known to promote the growth of the microorganism can be used concomitantly, For example, necessary nutrients may be added to the culture medium during the culture.

[Biosynthesis of Organic Compound]

The method for the biosynthesis of an organic compound according to one embodiment of the present invention comprises a step of reacting a first compound with a microorganism capable of producing a second organic compound from the first organic compound in the presence of an electrolyzed water. As the electrolyzed water, the electrolyzed water described above can be used. Preferably, in the reaction step, the culture medium constituting the habitat for the microorganism contains the electrolyzed water in an amount of not less than 10 wt %, more preferably, not less than 60 wt %, based on the total weight of the culture medium.

The microorganism used herein must be capable of growing in a culture medium containing the electrolyzed water as described above and biosynthesizing the second organic compound from the first organic compound. Such microorganisms are mainly divided into two types. One type is those constitutively expressing the ability to convert the first organic compound to the second organic compound and another type is those which express the ability inducibly (only in the presence of an inducer).

Strain JM1,(FERM BP-5352), and strain JM2N (FERM BP-5961), for example, are constitutively expressing the ability to form indigo (the second organic compound) from indole (the first organic compound). Therefore, they are suitably usable for the present embodiment.

Strain J1 (FERM BP-5102), is a microorganism capable of expressing the substance-converting ability inducibly. When this strain is used in the present embodiment, it is preferable to use cells grown with a carbon source and an inducer (e.g. an aromatic compound such as phenol or toluene) for the reaction with the first organic compound.

The bacteriological characteristics of strain JM1 are as follows:

Gram staining and morphology: Gram-negative rod
Growth condition in each medium
  BHIA: good
  MacConkey: possible
Color of colony: cream
Optimum growth temperature: 25° C.>30° C.>35° C.
Motility: negative (in semisolid medium)
(TSI (slant/butt): alkali/alkali, H2S(−)
Oxidase: positive (weak)
Catalase: positive
Fermentation of sugars
  glucose: negative
  sucrose: negative
  raffinose: negative
  galactose: negative
  maltose: negative
Urease: positive
Esculin hydrolysis (β-glucosidase): positive
Nitrate reduction: negative
Indole productivity: negative
Glucose acidification: negative
Arginine dihydrase: negative
Gelatin hydrolysis (protease): negative
β-galactosidase: negative
Assimilation of each compound
  glucose: negative
  L-arabinose: negative
  D-mannose: negative
  D-mannitol: negative
  N-acetyl-D-glucosamine: negative
  maltose: negative
  potassium gluconate: negative
  n-capric acid: positive
  adipic acid: negative
  dl-malic acid: positive
  sodium citrate: positive
  phenyl acetate: negative The JM1 strain is capable of degrading chlorinated organic compounds without aromatic compounds such as phenol, toluene and cresol as an inducer. It was deposited on Jan. 10, 1995 in the National Institute of Bioscience and Human-Technology, Agency of Industrial Science and Technology (Deposit No.: FERM BP-5352) at 1–3, Higashi 1-chome, Tsukuba-shi, Ibaraki-ken, 305 Japan.

The microbiological characteristics of the JM2N strain are as follows:

Gram's staining and morphology: Gram-negative, rods
Growth on culture medium:
  BHIA: good
  MacConkey: possible
Color of colony: creamy color
Optimum temperature: 25° C.>30° C.>35° C.
Motility: negative (in semi-solid medium)
TSI (slant/butt): alkali/alkali, H2S (−)
Oxidase: positive (weak)
Catalase: positive
Fermentation of sugars
  glucose: negative
  sucrose: negative
  raffinose: negative
  galactose: negative
  maltose: negative
Urease: positive
Esculin hydrolysis (β-glucosidase): positive
Silver nitrate reduction: negative
Indole production: negative
Glucose oxidation: negative
Arginine dihydrolase: negative
Gelatin hydrolysis (proteinase): negative
β-galactosidase: negative
Assimilation of each compound
  glucose: negative
  L-arabinose: negative
  D-mannose: negative
  D-mannitol: negative
  N-acetyl-D-glucosamine: negative
  maltose: negative
  potassium glucuronate: negative
  n-capric acid: positive
  adipic acid: negative
  dl-malic acid: positive
  sodium citrate: positive
  phenyl acetate: negative Strain JM2N (FERM BP-5961) was deposited on Jun. 13, 1996 in the National Institute of Bioscience and Human Technology, Agency of Industrial Science and Technology at 1–3, Higashi 1-chome, Tsukuba-shi, Ibaraki-ken, 305 Japan.

The bacteriological characteristics of the J1 strain are as follows:

Morphology
  Gram stain: positive
  Size and shape of cell: Pleomorphic rod of about 0.5–2 μm by 1–6 μm.
  Mobility: Non-mobile
  Colony: Sticky, creamy to light pink in color
Growth in culture media
  BIIIA: Good growth
  MacConkey: No growth
Optimum growth temperature: 25° C.>30° C.>35° C.
Physiological characteristics
  Aerobic/Anaerobic: Aerobic
  TSI (slant/stub): Alkali/alkali, H2S (−)
  Oxidase: negative
  Catalase: positive Fermentation of sugars
glucose: negative
sucrose: negative
raffinose: negative
galactose: negative
maltose: negative
Urease: positive
Esculin: positive
Nitric acid: negative This strain has an excellent ability to degrade chlorinated organic compounds. It was deposited in the National Institute of Bioscience and Human Technology, Agency of Industrial Science and Technology (Deposition No. FERM BP-5102) at 1–3, Higashi 1-chome, Tsukuba-shi, Ibaraki-ken, 305 Japan, on May 17, 1995.

In this embodiment, the reaction step of the microorganism and the first organic compound may be carried out in the presence of a carbon source or, a carbon source and an inducer, to allow the microbial growth and the production of the second organic compound. This enables more efficient synthesis of the second organic compound. The present inventors, incidentally, have found that when a certain combination of the microorganism and the carbon is used, the microbial growth may reduce the conversion rate of the first organic compound to the second organic compound. In the case of strain JM1, for example, the growth of this organism on sodium malate or sodium glutamate does not inhibit the synthesis of the second organic compound. However, the presence of sodium lactate or sodium pyruvate reduce the synthesizing ability. Therefore, it is preferable to decide whether the carbon source should be present in the reaction step or not, considering the combination of the microorganism and the carbon source to be used.

Alternatively, the microorganism is first grown in a growth medium containing the electrolyzed water and then cells are collected and transferred to the reaction medium containing the first organic compound where the second organic compound can be efficiently synthesized. This utilizes the fact that the presence of the electrolyzed water brings about an increase in the growth rate and the maximum cell number in the culture as described above. In this case, it is also preferable to avoid the carbon source which may reduce the conversion ability of the microorganism. When strain JI, JM1, or JM2N is concerned, it is preferable to use sodium malate or sodium glutamate.

[Method for Maintaining Microbial Ability to Decompose Pollutant/method for Decomposition of Pollutant/method for Restoration of Environment]

According to one embodiment of the present invention, the pollutant-decomposing ability of a microorganism can last long by culturing a microorganism having the pollutant-degrading ability in a culture medium containing the electrolyzed water obtained by electrolysis of water in an electrolytic cell.

According to one embodiment of the present invention, decomposition of a pollutant is accelerated by contacting a pollutant-decomposing microorganism with the pollutant to be decomposed in the presence of the electrolyzed water obtained by electrolysis of water in an electrolytic cell.

According to one embodiment of the present invention, effective remediation of an environment can be accomplished by contacting a pollutant-decomposing microorganism with the pollutant in the environment in the presence of the electrolyzed water obtained by electrolysis of water in an electrolytic cell.

As the electrolyzed water used in the above three embodiments, the same electrolyzed water as described above can be used. In any of the embodiments mentioned above, it is preferred that the electrolyzed water is contained in an amount of not less than about 10 wt %, more preferably not less than 60 wt %, based on the total weight of the culture medium which constitutes the habitat for the microorganism.

The suitable microorganisms to be used herein are those having a pollutant-decomposing ability and capable of proliferating in a culture medium containing the electrolyzed water. The microorganisms which can decompose a pollutant are mainly divided into two types. One type is those constitutively expressing the decomposing ability and another type those express the ability by induction (express the ability only when grown in the presence of an inducer). Both types can be used in the three embodiments mentioned above.

For example, in order to maintain the decomposing-ability of the inducible type of microorganisms, it is preferable that the microorganism is grown in the presence of an inducer and then cultured in a medium containing the electrolyzed water. Alternatively, the medium containing the electrolyzed water may further contain an inducer and a carbon source. When the culture medium contains the inducer and the carbon source, the combination of the microorganism and the carbon source should be suitably selected to avoid the reduction of the maintenance effect of the electrolyzed water by the growth of the microorganism.

By the same token, when a microorganism requiring an inducer is used in the method for the decomposition of a pollutant or in the method for the environmental remediation mentioned above, it is preferable that the microorganism is preparatorily grown in the presence of an inducer and then contacted with the pollutant in a medium containing the electrolyzed water, or it is preferable to contact the microorganism with the pollutant in the presence of the electrolyzed water, the inducer, and a carbon source. When the contact of the pollutant with the microorganism is carried out in the presence of the electrolyzed water, the inducer, and the carbon source, it is preferable that the combination of the microorganism with the carbon source is properly selected so as not to spoil the improved decomposition efficiency due to the electrolyzed water.

In the case that the microorganism constitutively expressing the decomposing ability is employed for the method for the maintenance of the pollutant-decomposing ability, it is preferable to culture the microorganism in a culture medium containing the electrolyzed water but no carbon source or in a culture medium containing both the electrolyzed water and a carbon source. When the microorganism constitutively expressing the decomposing ability is used in the method for the decomposition of a pollutant or the method of the remediation of an environment mentioned above, it is preferable that the microorganism is brought into contact with the pollutant in the presence of the electrolyzed water or in the presence of the electrolyzed water and a carbon source. When the carbon source is present, however, it is preferable that the combination of the microorganism and the carbon source is properly selected not to spoil the improving effect of the electrolyzed water.

Examples of the microorganisms having the inducible activity to decompose aromatic compound such as phenol, toluene and cresol, or decompose halogenated aliphatic hydrocarbons such as TCE or DCE, include *Pseudomonas cepacia* KK01 (FERM BP-4235) and strain J1 (FERM BP-5102). An aromatic compound such as phenol and toluene, or methane serves as an inducer for these microorganisms.

Further examples of the microorganisms constitutively expressing the ability for decomposing the same pollutants as mentioned above include Strain JM1 (FERM BP-5352), and strain JM2N (FERM BP-5961). Sodium malate and sodium glutamate are the preferable carbon source for these strains, since their coexistence does not spoil the effect of the electrolyzed water.

[Method for Remediation of Environment]
[Medium]

Now, the method for the decomposition of a pollutant and the method for the remediation of an environment are described in detail. In these methods the pollutant is made into contact with a microorganism. Specifically, a medium containing the pollutant is introduced into a reaction vessel containing the microorganism and the electrolyzed water, alternatively, a medium containing the microorganism and the electrolyzed water is introduced directly into the environment. Here the medium includes an aqueous medium into which the pollutant has dissolved, and the environment includes the ground water contaminated with the pollutant. As another example of the medium, there is a solid substance to which the pollutant has adsorbed. Corresponding example of an environment is the soil to which the pollutant has adsorbed. As yet another example of such a medium, there is a gas containing the pollutant. A corresponding example of such an environment is air containing the pollutant.

When the pollutant is contained in an aqueous medium or the environment to be treated is an aqueous medium such as ground water, the contact of the pollutant in the medium with the microorganism can be achieved, for example, by directly introducing the microorganism with a water containing the electrolyzed water into the aqueous medium. In this case, since the electrolyzed water is diluted with the aqueous medium subjected to the treatment, it is preferable to determine the amount of the electrolyzed water to be introduced to ensure the effect of the electrolyzed water on the microorganism.

The contact between the pollutant in the aqueous medium and the microorganism may be carried out by a) culturing the microorganism in a culture tank in the presence of the electrolyzed water and introducing into the culture tank the aqueous medium containing the pollutant;

b) culturing the microorganism in a culture tank in the absence of the electrolyzed water and introducing into the culture tank the water containing the electrolyzed water and an aqueous medium containing the pollutant; or c) culturing the microorganism in a culture tank in the absence of the electrolyzed water, transferring the cultured microorganism to a reaction tank containing a culture medium containing the electrolyzed water, and continuing the cultivation and meanwhile introducing therein an aqueous medium containing the pollutant.

Feeding and discharging of the aqueous medium into and out of the culture tank or the reaction tank may be done continuously, batch-wise, or intermittently, depending on the treatment capacity. With any method of feeding and discharging, it is preferable to keep constant the concentration of the culture medium containing the electrolyzed water in the culture tank or the reaction tank.

Alternatively, a microorganism is attached to a carrier, which is introduced into the reaction tank containing the electrolyzed water, and the aqueous medium containing the pollutant is introduced into the reaction tank for decomposition. Preferable carriers to be used herein are those good at retaining the microorganism thereon and do not reduce the aeration efficiency. As examples of such a carrier, there are inorganic particles such as porous glass, ceramics, metal oxides, active carbon, kaolinite, bentonite, zeolite, silica gel, alumina, and anthracite, gelated carriers such as starch, agar, chitin, chitosan, polyvinyl alcohol, alginic acid, polyacryl amide, carrageenan, agarose, and gelatin, and ion-exchanging cellulose, ion-exchange resins, cellulose derivatives, glutar aldehyde, polyacrylic acid, polyurethane, and polyesters. As a natural carrier, there are soil particles, cellulosic substances such as cotton, hemp, and paper, and ligneous substances such as wood powder and tree barks.

[Solid Phase (Soil)]

When the pollutant is contained in a solid material or the environment to be treated is a solid matter such as a polluted soil, the contact between the pollutant in the solid and a microorganism may be carried out, for example, by directly introducing into the solid matter the microorganism with water containing the electrolyzed water.

When the pollutant is contained in a soil, the microorganism is introduced into the soil with a culture medium containing the electrolyzed water, for example, by spraying them on the surface of the soil or by introducing them into the ground via a pipe inserted in the soil.

[Gaseous Phase (Air)]

When the pollutant is contained in a gas or the environment to be treated is a gas such as air, the contact between the pollutant in the gas and the microorganism may be accomplished, for example, by introducing the gas into a reaction tank containing the microorganism and water containing the electrolyzed water.

Although no limit is imposed on the method of introducing the gas, it is preferable that the introduction of the gas promotes the aeration of the microorganism and the water containing the electrolyzed water in the reaction tank by stirring. The gas may be continuously introduced into and discharged from the reaction tank, or may be introduced intermittently or batchwise, depending on the capacity of the microorganism to treat the pollutant or the concentration of the pollutant.

In the various forms of reaction mentioned above, it is desirable to control the ambient conditions (e.g. pH, salt concentration, temperature, and concentration of a pollutant) for the microorganism during the decomposition of the pollutant. However, in the remediation of an environment, it is often difficult to set the optimum conditions for the activity of the microorganism. Surprisingly, the present invention which uses the electrolyzed water enables the efficient decomposition of the pollutant and remediation of the environment even when these conditions are extremely harsh for the microorganism. For example, strain JM1, and strain JM2N, i.e. the microorganisms that can be used in the various embodiments of this invention mentioned above, possess an extraordinarily excellent property of being capable of decomposing aromatic compounds such as phenol, toluene, and cresol and halogenated aliphatic hydrocarbons such as TCE and DCE without requiring an inducer. For these microorganisms, suitable culture temperature is about 15–30° C. At a low temperature, for example, as low as 4° C., it is difficult for them to decompose a pollutant. However, with the presence of the electrolyzed water according to the present invention, the microorganism can decompose the pollutant even under the harsh condition of 4° C. for any microorganism. Consequently, it will loosen the conditions for the decomposition of the pollutant to widen the ranges of application of the microbial decomposition of a pollutant in an aqueous medium or the microbial remediation of the aqueous medium, as compared with the conventional treatment.

According to the various embodiments of this invention, following results can be achieved.

1) The growth rate of a microorganism and the maximum cell number in the culture can be increased.

2) In the production of a substance by the use of a microorganism, the productivity can be improved.

3) It is possible to maintain for a long period of time the inducible or constitutive ability of a microorganism to decompose organic compounds such as aromatic compounds and halogenated aliphatic hydrocarbon compounds.

4) The efficiency of decomposition of the pollutant can be further improved.

5) The remediation of a polluted environment can be achieved more efficiently.

Such advantageous effects are believed to widen further the range of application of microbial production or microbial remediation of an environment.

Now, the embodiments of this invention will be described more specifically with reference to working examples of the invention.

EXAMPLES

The microorganisms which were used in the working examples were, a bacterial strain (strain J1 (FERM BP-5102) which can metabolize aromatic compounds and decompose organic chlorine compounds such as TCE, mutant strains derived from strain J1, strain JM1 (FERM BP-5352) and strain JM2N (FERM BP-5961 which can express the decomposing ability of organic chlorine compounds constitutively, that is, without any inducer, and *Escherichia coli* JM109 (a product of Toyobo K.K. under a trade name of "Competent Cell Kit Code No. DNA-900"), a popular strain in genetic engineering.

Example 1

Preparation of Electrolyzed Water-containing M9 Medium

Acidic water and alkaline water which were used in the experiments were manufactured using an electrolyzed water production device (a product of Asahi Glass Engineering Co., Ltd. under a trade name of "Oasis Biohalf OW-OH"). Before use, the acidic water was stirred in a beaker using a stirrer under UV irradiation, to reduce the dissolved chlorine concentration less than 0.3 ppm. The alkaline water was used without further processing.

Into water containing acidic water or alkaline water at 50% or 100%, salts of M9 medium components were dissolved at concentrations to form M9 medium mentioned above. The resultant solutions were passed through a filter of 0.22 µm pore size for sterilization, and used as electrolyzed water-containing M9 media (hereinafter referred to as 50% or 100% acidic water M9 medium and 50% or 100% alkaline water M9 medium). At the point when the salts were dissolved, pH of the solutions were in the approximate range of 6.5–7.5 and redox potentials about 300 mV (200 mV–400 mV).

(1) Effect of Alkaline Water on Viable Cell Ratio of Strain JM1-(1)

Figure 2:
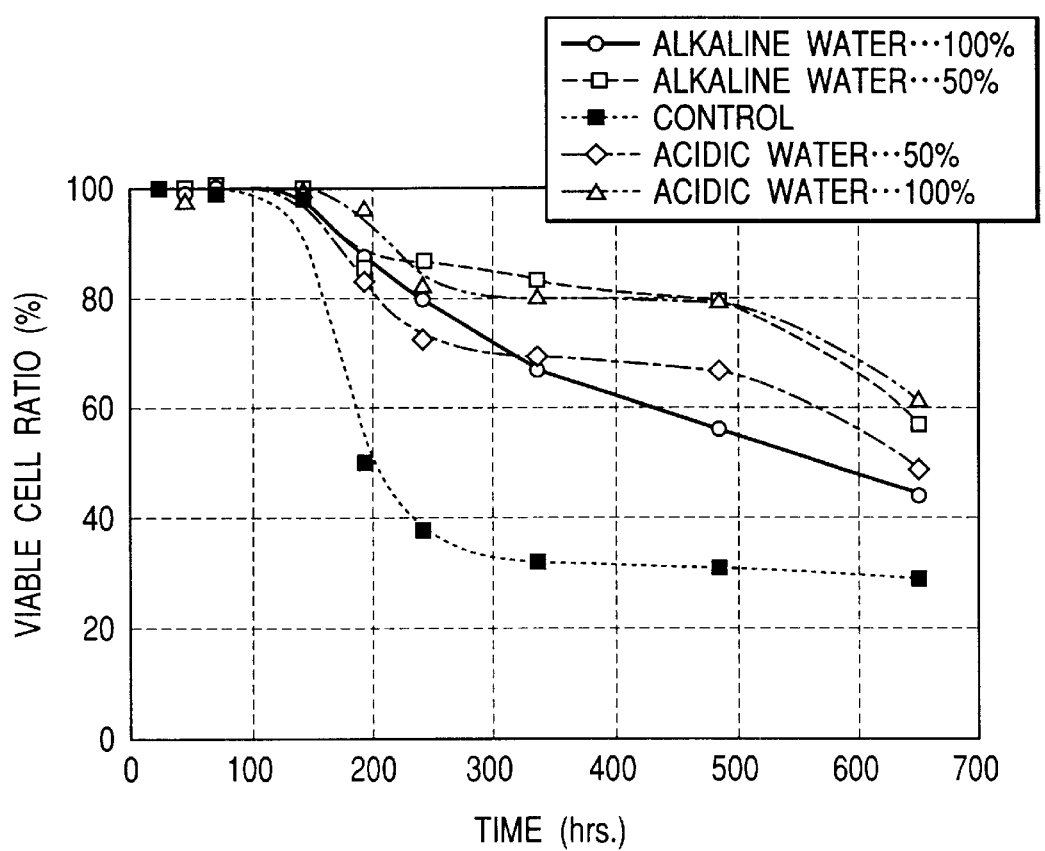
FIG. 2 is a graph to show the viability of strain JM1 in Example 1, where strain JM1 was cultured at 15° C. in an M9 medium containing a carbon source and the alkaline water, in an M9 culture medium containing a carbon source and the acidic water, and in a control medium.

Two 50 ml test tubes (a product of GREINER LABORTECHNIK) were prepared, and then 50% alkaline water M9 medium and 100% alkaline water M9 medium each containing 1% of malic acid were put into the tubes respectively. The tubes were inoculated with a colony of strain JM1 grown on an agar medium and then subjected to shaking culture at 15° C. Periodically, 10 µl aliquots were taken from each of the tubes, 10-fold diluted with distilled water, to which 0.3 µl of LIVE/DEAD BacLight Viability Kit (a product of Molecular Probes, Inc., U.S.A.) was added to detect both viable cell number and total (dead or alive) cell number simultaneously. Staining was carried out at room temperature for about 30 minutes. Total cell concentration and viable cell concentration were determined by flow cytometry, using FACScan (a product of Becton Dickinson Corp., U.S.A.). The time-course change of the viable cell ratio, i.e. the ratio of the viable cell number to the total cell number is shown in FIG. 2.

It was found that alive and metabolically active cells were 55.6% of the total cells of strain JM1 in 100% alkaline water M9 medium and 78.6% in the 50% alkaline water M9 medium after about 20 days of culture, and 42.7% and 56.6% after about 27 days, respectively.

(2) Effect of Acidic Water on Viable Cell Ratio of Strain JM1-(1)

The time-course change of the viable cell ratio was determined in the same manner as in above (1), except that 50% and 100 acidic water M9 media were used instead of the 50% and 100% alkaline water M9 media. As shown in FIG. 2, it was found that alive and metabolically active cells were 78.7% of the total cells of strain JM1 in 100% acidic water M9 medium and 65.8% in 50% acidic water M9 medium respectively after about 20 days of culture, and 60.9% and 47.5% after about 27 days respectively.

(3) Control

The time-course change of the viable cell ratio was determined in the same manner as in (1), except that 1% malic acid-containing M9 medium prepared using distilled water instead of 50% alkaline water was used. As shown in FIG. 2, it was found that the average viable cell ratio lowered to 33.4% after about 14 days of culture.

Example 2

(1) Effect of Alkaline Water on Viable Cell Ratio of Strain JM1-(2)

Figure 3:
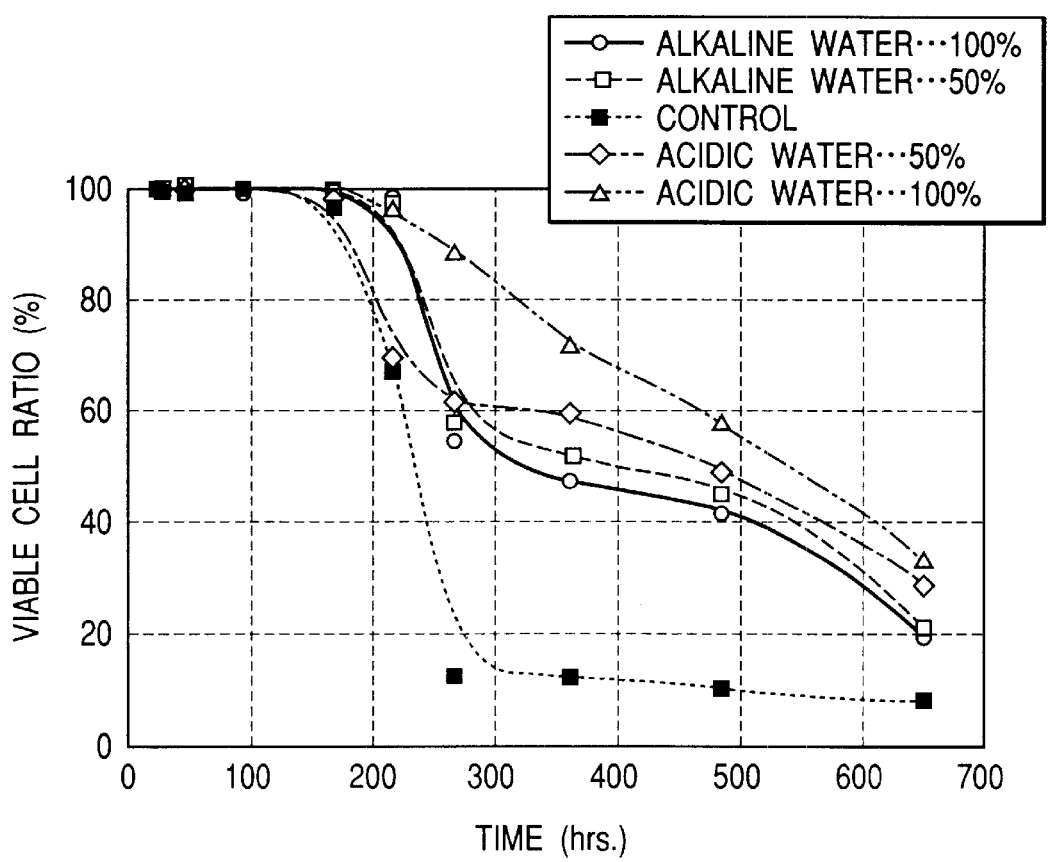
FIG. 3 is a graph to show the viability of strain JM1 in Example 2, where strain JM1 was cultured at 25° C. in an M9 medium containing a carbon source and the alkaline water, in an M9 culture medium containing a carbon source and the acidic water, and in a control medium.

The time-course change of the viable cell ratio was determined by the same manner as in Example 1-(1) except that the shaking culture was carried out at 25° C. As shown in FIG. 3, it was found that alive and metabolically active cells were 42.6% of the total cells of strain JM1 in 100% alkaline water M9 medium and 46.2% in 50% alkaline water M9 medium after about 20 days of culture, and 18.9% and 21.2% after about 27 days respectively.

(2) Effect of Acidic Water on Viable Cell Ratio of Strain JM1-(2)

The time-course change of the viable cell ratio was determined, in the same manner as in Example 1-(2) except that the shaken culture was carried out at 25° C. As shown in FIG. 3, it was found that alive and metabolically active cells were 57.7% of the total cells of strain JM1 in 100% acidic water M9 medium and 49.1% in 50% acidic water M9 medium respectively after about 20 days of culture, and 33.7% and 29.1% after about 27 days respectively.

(3) Control

The time-course change of the viable cell ratio was determined in the same manner as in Example 2-(1) except that 1% malic acid-containing M9 medium prepared using distilled water instead of acidic water was used. As shown in FIG. 3, it was found that the average viable cell ratio lowered to 14.2% after about 11 days of culture.

Example 3

Effect of Acidic Water, Alkaline Water, and Mixture Thereof on Growth of Strain J1

A colony of strain J1 grown on M9 agar medium containing 1.0% sodium malate was transferred to 200 ml of M9 medium containing 1.0% sodium malate in a 500 ml shaking culture flask, and subjected to shaking culture at 15° C. for three days.

Then, four 50 ml culture tubes containing 10 ml of four culture media respectively (culture tubes a–d) were prepared. These culture media had been sterilized by filtration.

- Culture tube (a): 1% sodium malate-containing M9 medium which was prepared by diluting×10 (10-fold conc.) M9 medium with dechlorinated acidic water prepared in Example 1.
- Culture tube (b): 1% sodium malate-containing M9 medium which was prepared by diluting×10 M9 medium with alkaline water prepared in Example 1.
- Culture tube (c): 1% sodium malate-containing M9 medium which was prepared by diluting×10 M9 medium with 1:1 (v/v) mixture of dechlorinated acidic water and alkaline water prepared in Example 1.
- Culture tube (d): 1% sodium malate-containing M9 medium which was prepared by diluting×10 M9 medium with deionized water.

The culture tubes (a)–(d) were inoculated with 0.1 ml of the above mentioned culture of strain J1, and subjected to shaking culture at 15° C.

Figure 4:
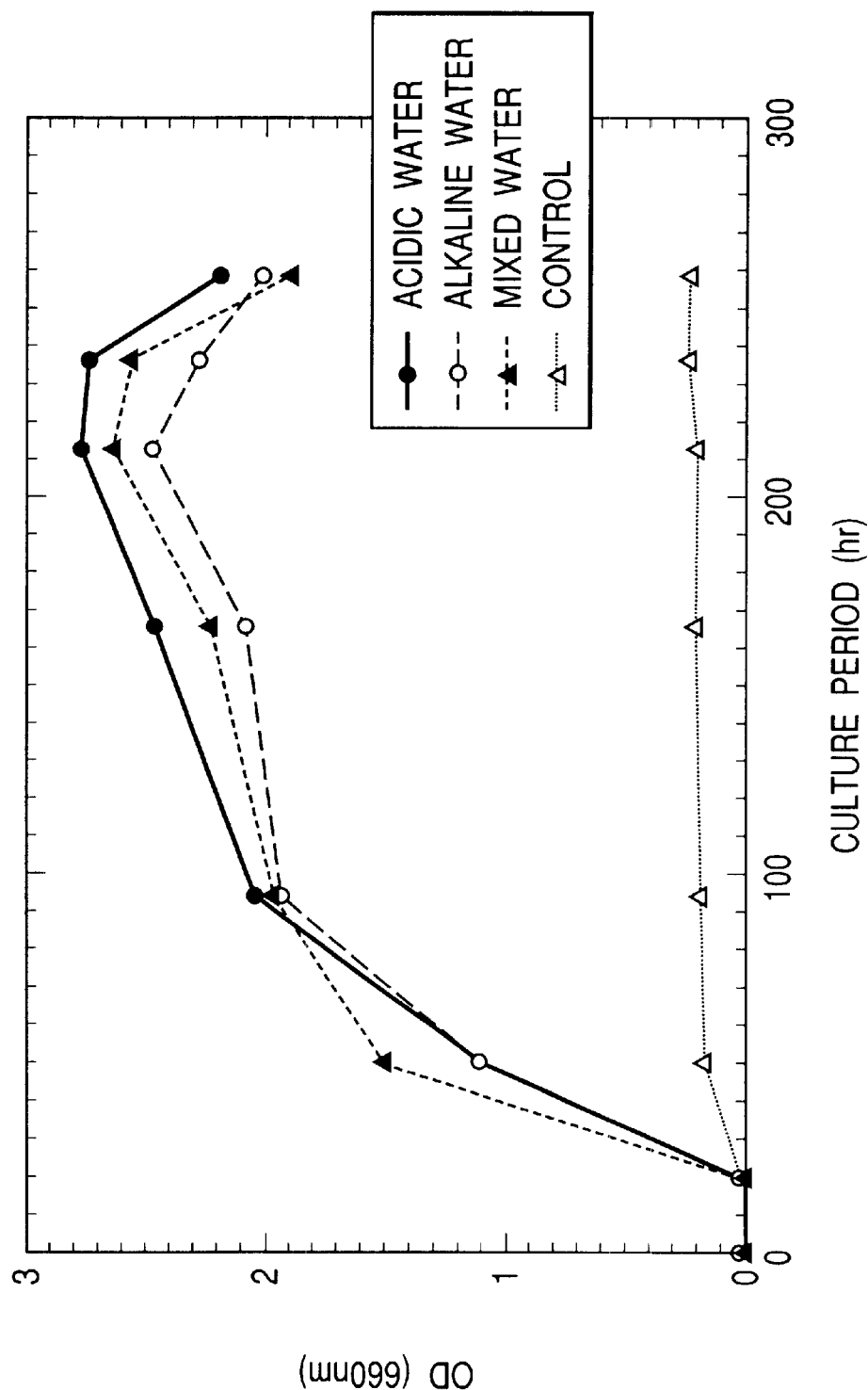
FIG. 4 is a graph to show the growth rate and maximum cell density of J1 in Example 3 when cultured in various culture media.

The culture was periodically sampled to measure the turbidity (OD) at 660 nm using a spectrophotometer (a product of Masuda Rikakogyo K.K. under the trade name of "SMART PLUS 3255"). The results are shown in FIG. 4. When OD was higher than 0.5, samples were diluted 3-fold and the OD of the dilution was multiplied by three.

Cultures of strain J1, in the culture tubes (a)–(c) all showed notable improvements in both growth rate and maximum cell number as compared with the culture in (d).

Example 4

Effect of Acidic Water, Alkaline Water, and Mixture Thereof on Growth of Strain JM1

Figure 5:
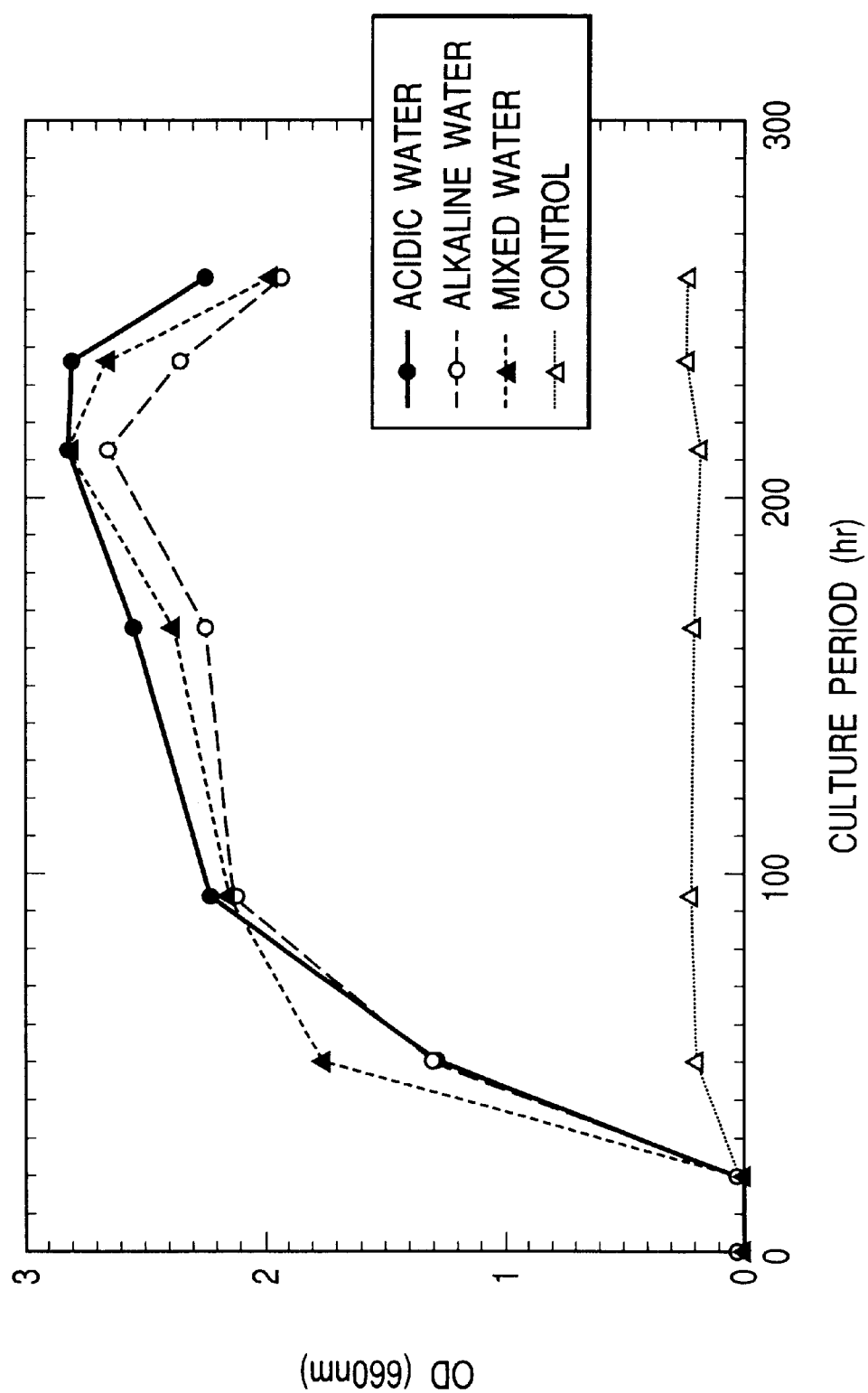
FIG. 5 is a graph to show the growth rate and maximum cell density of JM1 in Example 4 when cultured in various culture media.

The growth rate and the maximum cell number of strain JM1 were determined in the same manner as in Example 3 except that strain JM1 was used instead of strain J1. As shown in FIG. 5, culture of strain JM1 in the culture tubes (a)–(c) all showed notable improvement in both growth rate and maximum cell number as compared with the culture tube (d).

Example 5

Figure 6:
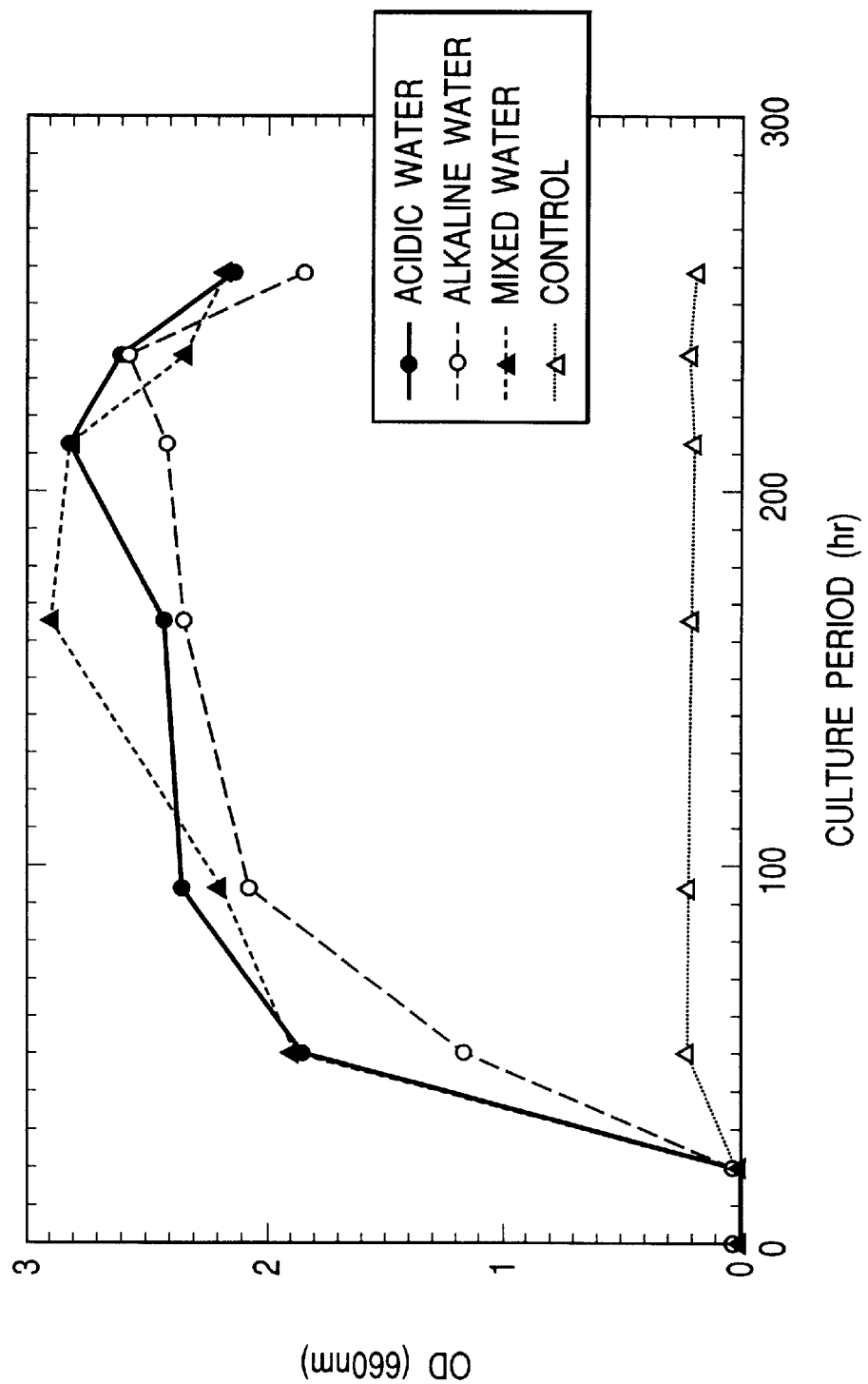
FIG. 6 is a graph to show the growth rate and maximum cell density of JM2N in Example 5 when cultured in various culture media.

Effect of Acidic Water, Alkaline Water, and Mixture Thereof on Growth of Strain JM2N The growth rate and the maximum cell number of strain JM2N were determined in the same manner as in Example 3 except that strain JM1 (FERM BP-5961) was used in the place of strain J1. As shown in FIG. 6, culture of strain JM2N in the culture tubes (a)–(c) all showed notable improvement in both growth rate and maximum cell number as compared with the culture tube (d).

Example 6

Effect of Acidic Water, Alkaline Water, and Mixture Thereof on Growth of *Escherichia coli* Strain JM109

A colony of strain JM109 grown on LB agar medium was transferred to 200 ml of M9 medium containing 1.0% glucose in a 500 ml shaking culture flask, and cultured with shaking at room temperature (23° C.) for three days.

Figure 7:
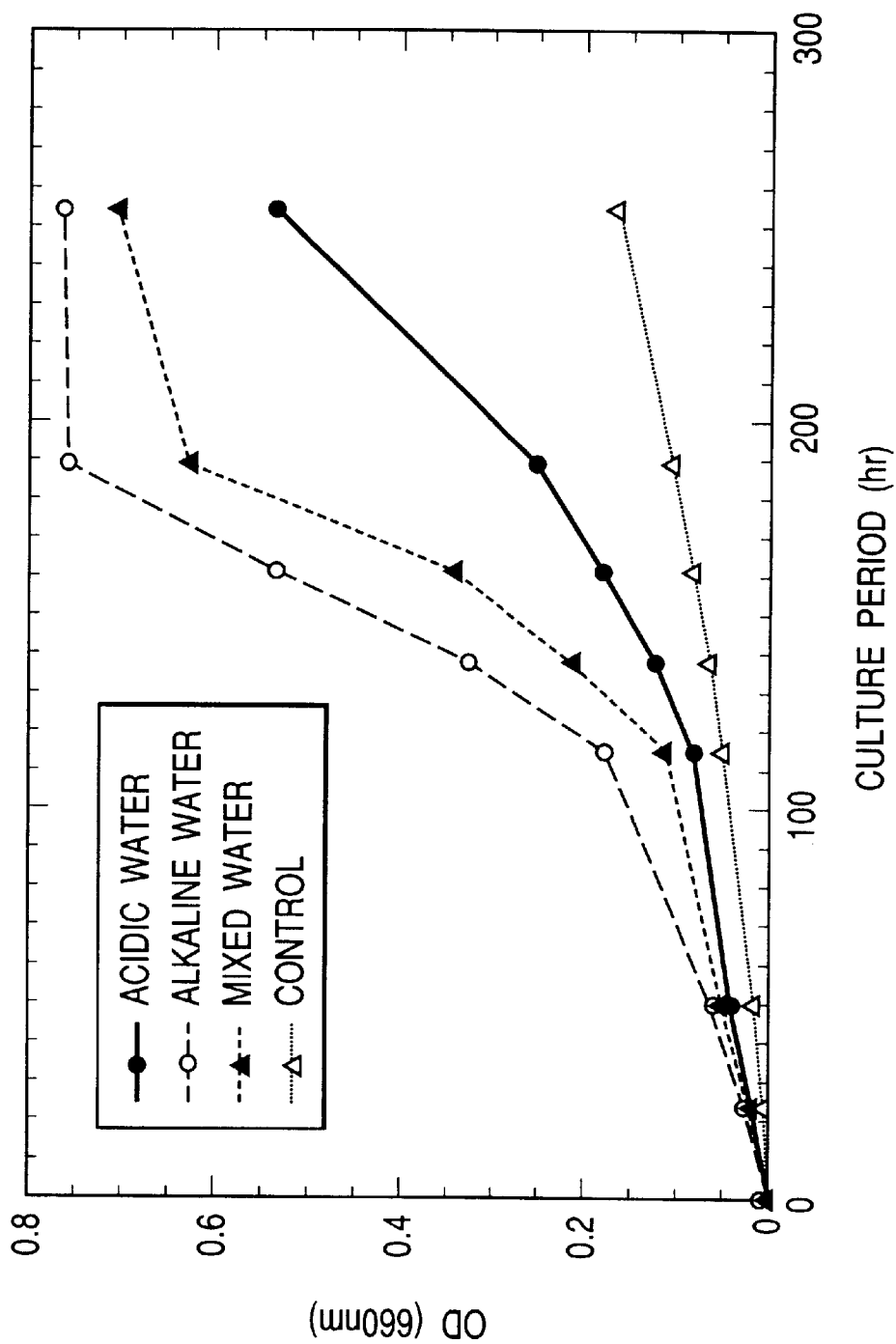
FIG. 7 is a graph to show the growth rate and maximum cell density of JM106 in Example 6 when cultured in various culture media.

Then culture tubes (a)–(d) were prepared in the same manner as in Example 3, except that 0.2% glucose was used as the carbon source instead of 1% sodium malate. The tubes were inoculated with 0.1 ml of above *E. coli* culture, and subjected to shaking culture at 15° C. Each culture was periodically sampled and turbidity (OD),was measured at 660 nm by means of a spectrophotometer (a product of Masuda Rikakogyo K.K. under the trade name of "SMART PLUS 3255"). The results are shown in FIG. 7.

*E. coli* JM109, as with strain JM1, showed notable improvements in both the growth rate and maximum cell number when cultured with acid water, alkaline water, or the mixture thereof, as compared with the control culture medium prepared with deionized water.

Example 7

Effect of Electrolyzed Water on Indigo Production by Strain JM1

100% acidic water M9 medium and 100% alkaline M9 medium were prepared in the same manner as in Example 1.

A colony of strain JM1 grown on an agar culture medium was inoculated to 100 ml of M9 medium containing 2% sodium malate. The culture was cultured with shaking in a shaking culture flask at 15° C. for 70 hours. Then, 45 ml aliquots of the culture were put in four sterilized 50 ml tubes, and centrifuged. After the removal of the supernatant, the pellets in four tubes were resuspended with 10 ml of following solutions respectively.

A: A normal M9 medium.
B: 9:1 mixture of 100% acidic water M9 medium and normal M9 medium.
C: 9:1 mixture of 100% alkaline water M9 medium and normal M9 medium.
D: 1:1 mixture of 100% acidic water M9 medium and 100% alkaline water M9 medium.

Indole was added to each tube to a final concentration of 1 mM and the resultant mixture was shaken at 25° C. for 24 hours. The mixture was assayed to determine the amount of indigo formed in accordance with the method proposed by Keil et al. (J. Bacteriol., 169, 764–770 (1987)). The amounts of indigo formed in the these samples are shown in relative values in Table 3, making the amount in the sample A 100.

TABLE 3

| Sample | Relative value of amount of indigo formed |
|---|---|
| A | 100 |
| B | 125 |
| C | 119 |
| D | 123 |

The result shows that the use of the electrolyzed water brought about a marked improvement in the productivity of indigo by strain JM1 as compared with the standard medium.

Example 8

Effect of Acidic Water on TCE Decomposition by Strain JM1-(1)

A colony of strain JM1 grown on an agar culture medium was transferred into 200 ml M9 medium containing 2.0% of sodium malate in a shaking culture flask, and subjected to shaking culture at 15° C. for 70 hours. Six 10 ml aliquots of the culture was centrifuged, and after removing the supernatant, each pellet was resuspended in 10 ml of an M9 medium containing 0 (control), 1, 5, 10, 20, or 50% of the acidic water. At this point, the cell concentration was $3 \times 10^8$ CFU/ml.

Figure 8:
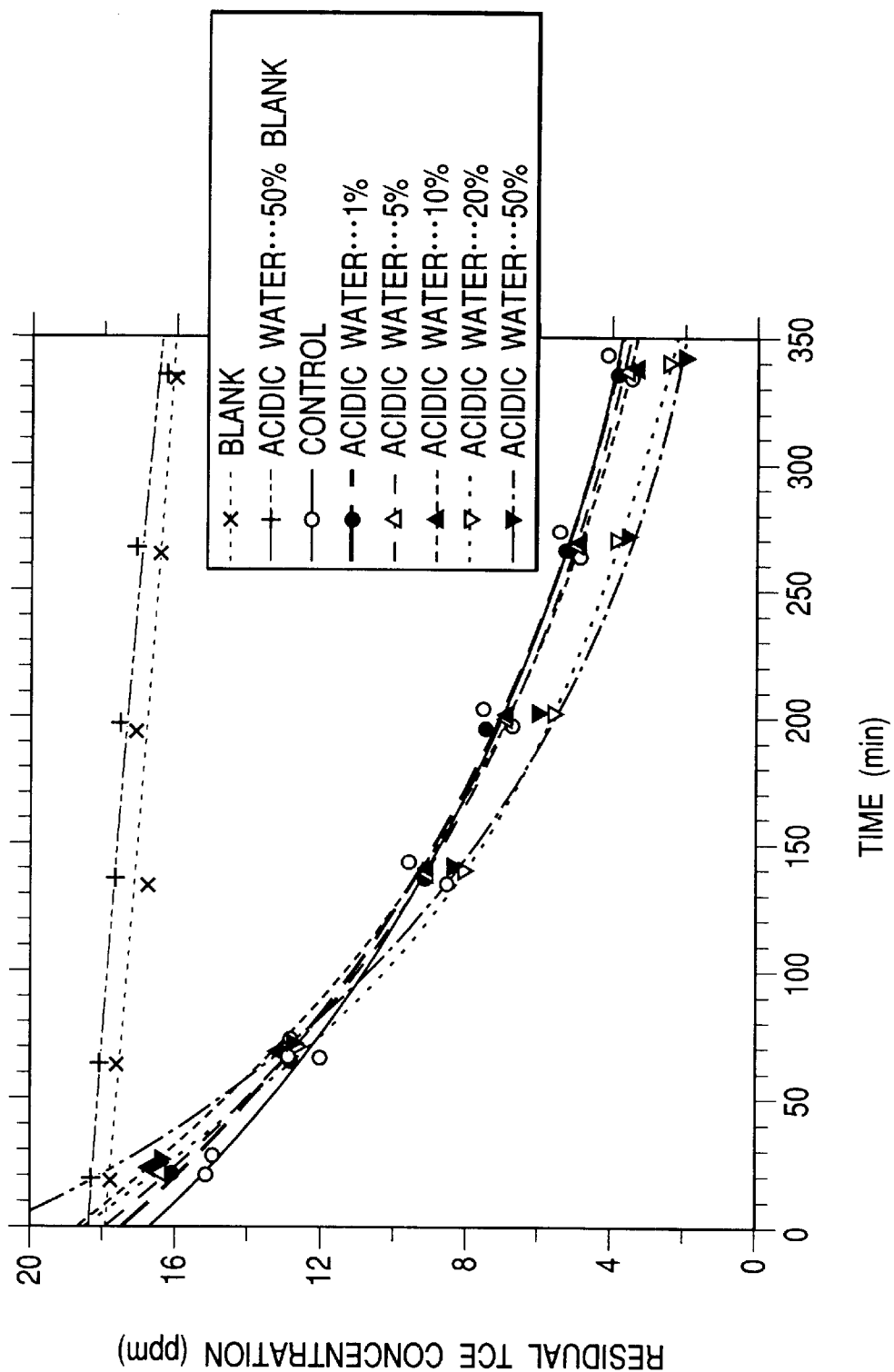
FIG. 8 is a graph to show the TCE degradation ability of strain JM1 in Example 8, where strain JM1 degraded TCE in the presence or absence of the acidic water.

The resultant suspensions were transferred severally into 27 ml vials, each of which was tightly sealed with a butyl rubber stopper and an aluminum cap. Then 1 ml of TCE-containing air was injected into each vial with a syringe. The TCE-containing air was prepared by placing 10 ml of an aqueous solution of 1000 ppm TCE in a 27 ml vial, and collecting the gaseous phase after one hour standing at 25° C. The vials are continuously shaken at 25° C. measuring the change of the TCE concentration in the gaseous phase in the vial by gas chromatography (an FID detector, GC-14B, Shimadzu Seisakusho Ltd.). Blank systems were those containing 0% and 50% of the acidic water but without addition of strain JM1. The results are shown in FIG. 8. The blanks containing 0% and 50% acidic water showed virtually no difference in TCE concentration, indicating the absence of TCE decomposition by the acidic water itself. The systems containing strain JM1, showed marked TCE decomposition at the acidic water contents of 20% and 50% as compared with the controls.

Example 9

Effect of Acidic Water on TCE Decomposition by Strain JM1 (2)

Figure 9:
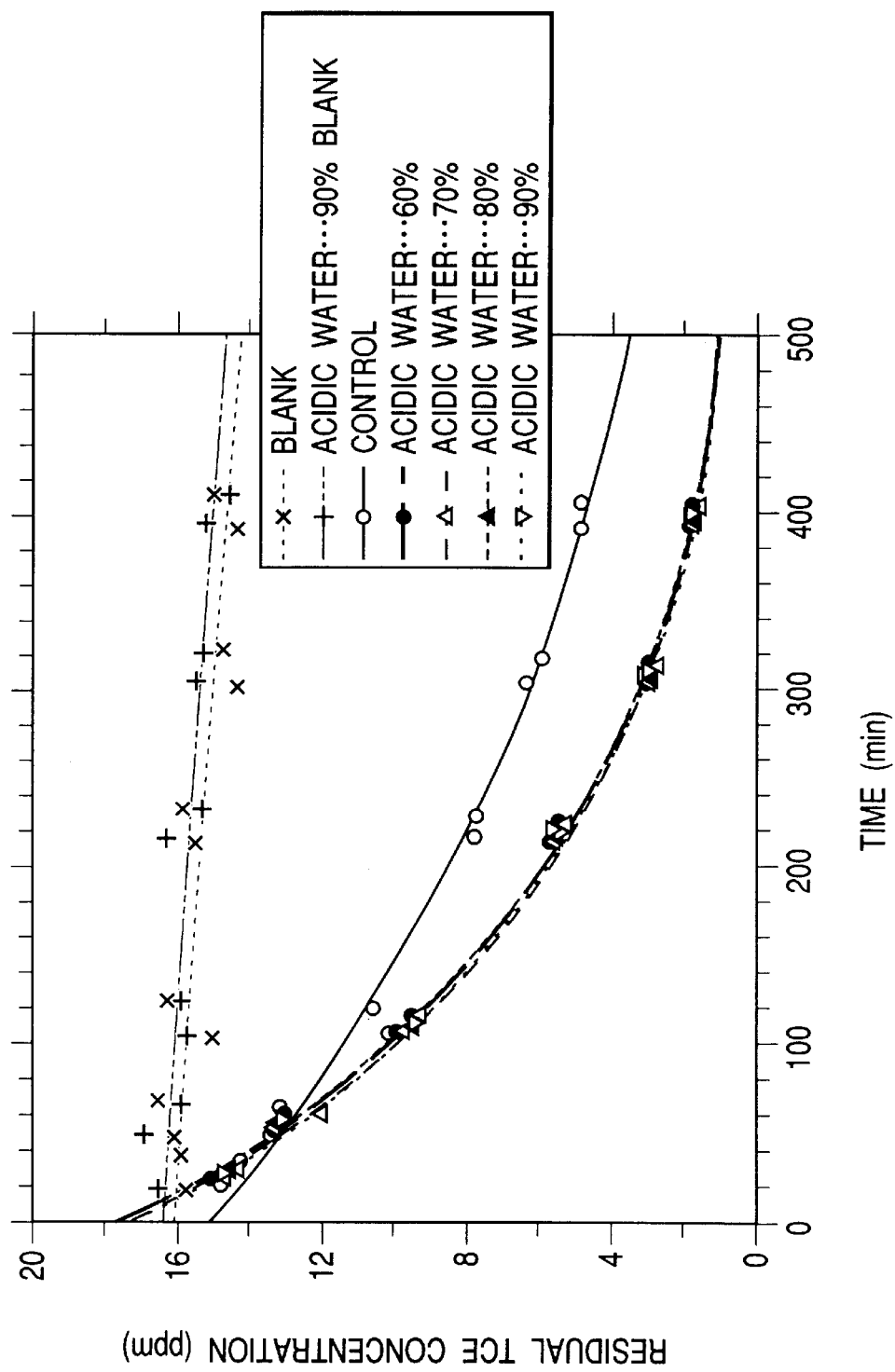
FIG. 9 is a graph to show the TCE degradation ability of strain JM1 in Example 9, where strain JM1 degraded TCE in the presence or absence of the acidic water.
Figure 10:
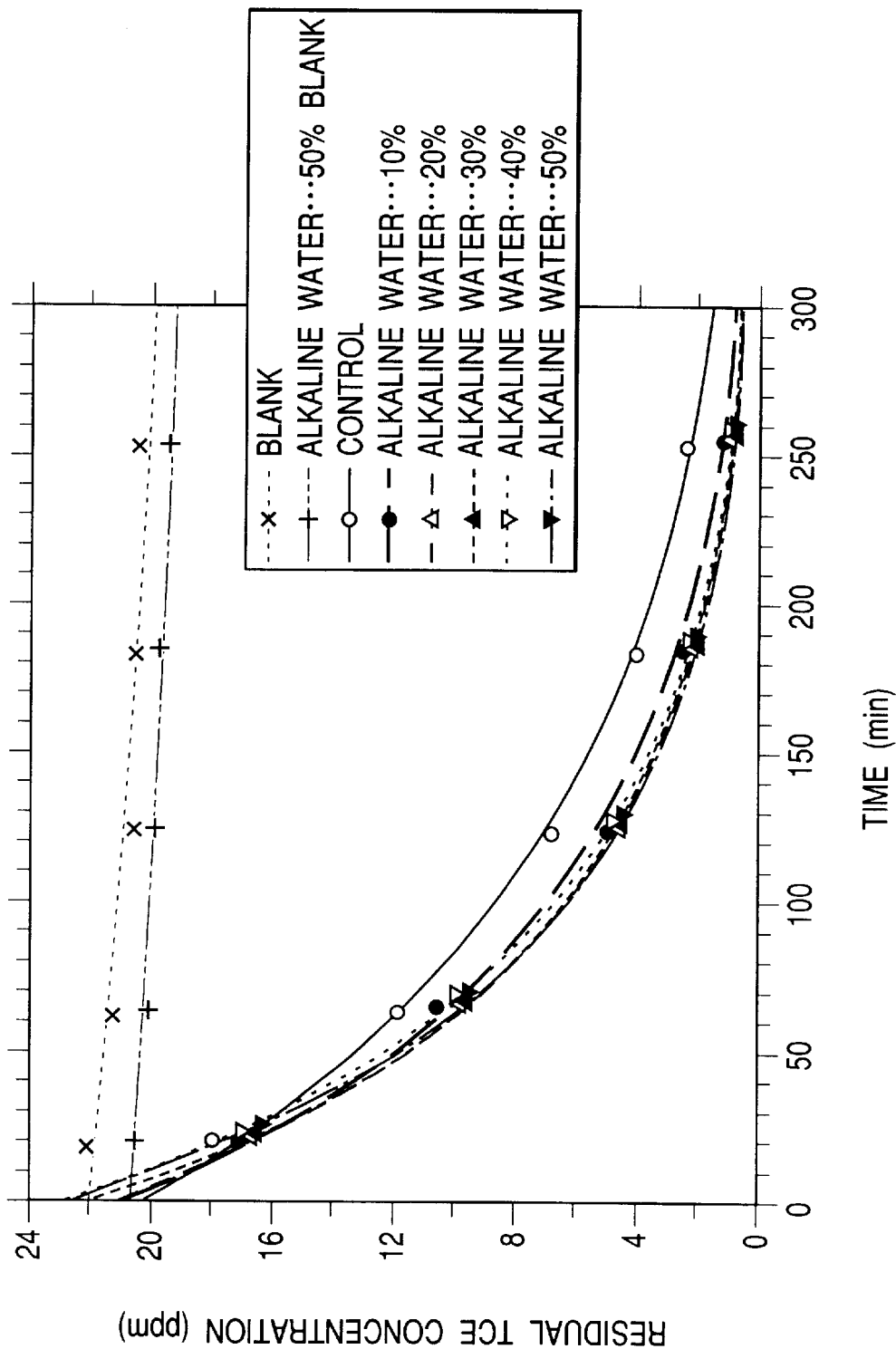
FIG. 10 is a graph to show the TCE degradation ability of strain JM1 in Example 10, where strain JM1 degraded TCE in the presence or absence of the alkaline water.

An experiment was carried out in the same manner as in Example 8 except that acidic water concentrations were 0 (control), 60, 70, 80, and 90%, and the blanks contained acidic water at concentrations of 0 and 90%. The results are shown in FIG. 9.

The blanks containing 0% and 90% acidic water showed virtually no difference in TCE concentration, indicating the absence of TCE decomposition by the acidic water itself. The systems containing strain JM1 and acidic water showed markedly accelerated TCE decomposition compared with the controls.

Example 10

Effect of Alkaline Water on TCE Decomposition by Strain JM1-(1)

An experiment was carried out in the same manner as in Example 8 except that alkaline water concentrations of 0 (control), 10, 20, 30, 40, and 50% were used, and the blanks contained alkaline water at concentrations of 0 and 50%. The results are shown in FIG. 9.

The blanks containing 0% and 50% alkaline water showed virtually no difference in TCE concentration, indicating the absence of TCE decomposition by the alkaline water itself. The systems containing strain JM1 and alkaline water more than 10% showed markedly accelerated TCE decomposition compared with the controls.

Example 11

Effect of Alkaline Water on TCE Decomposition by Strain JM1-(2)

Figure 11:
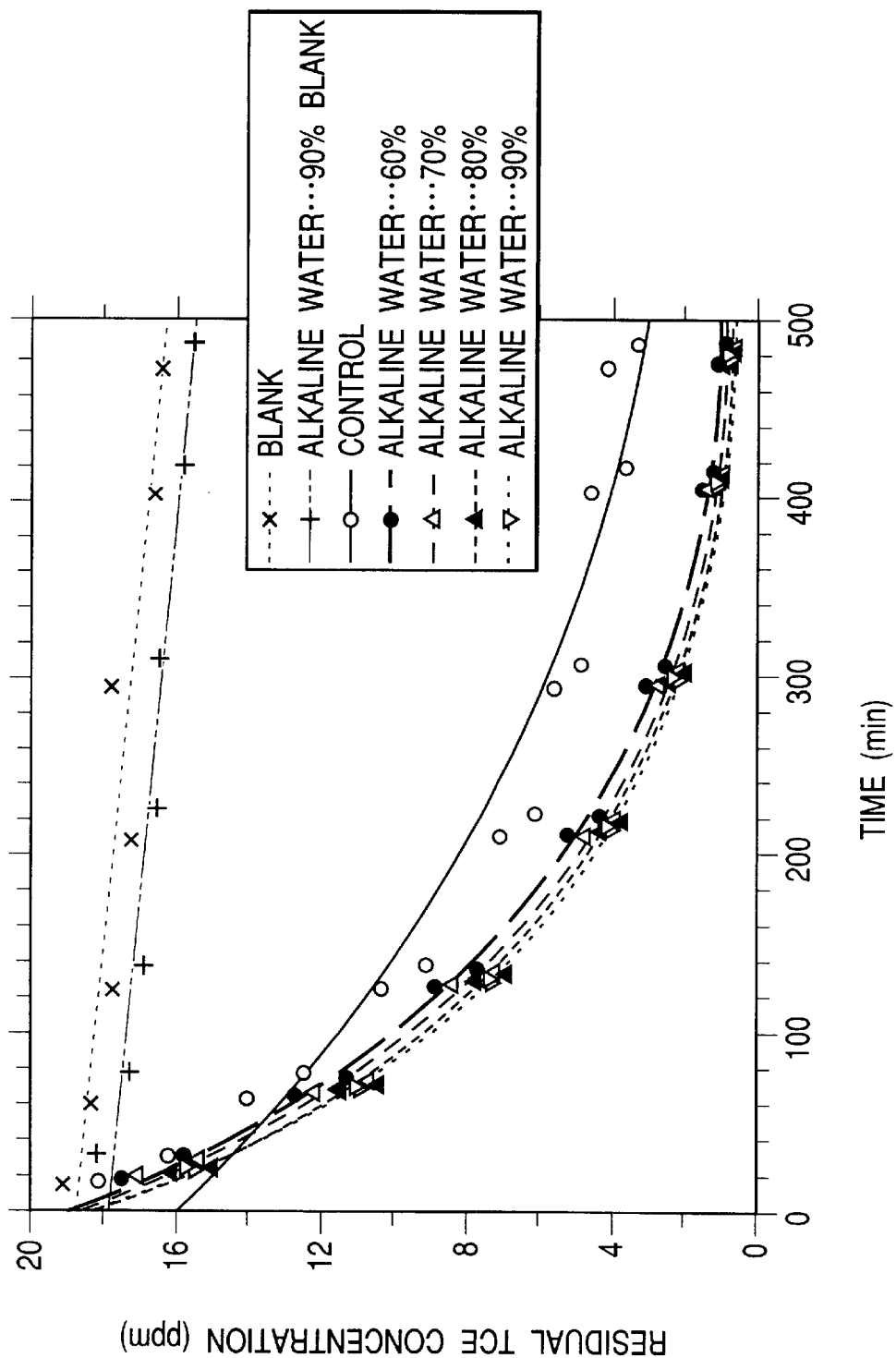
FIG. 11 is a graph to show the TCE degradation ability of strain JM1 in Example 11, where strain JM1 degraded TCE in the presence or absence of the alkaline water.

An experiment was carried out in the same manner as in Example 8 except that alkaline water concentrations of 0 (control), 60, 70, 80, and 90% were used, and the blanks contained alkaline water at concentrations of 0 and 90%. The results are shown in FIG. 11.

The blanks containing 0% and 50% alkaline water showed virtually no difference in TCE concentration, indicating the absence of TCE decomposition by the alkaline water itself. The systems containing strain JM1 and alkaline water more than 10% showed markedly accelerated TCE decomposition compared with the controls.

Example 12

Effect of Acidic Water on DEC Decomposition by Strain JM1

An experiment was carried out in the same manner as in Example 9 except that 1,1-DCE (1,1-dichloroethylene), cis 1,2-DCE (cis 1,2-dichloroethylene), and trans 1,2-DCE (trans 1,2-dichloroethane) were used as the substances to be decomposed. These substances were added as a gas-in-air as with TCE and the initial concentrations were 5 ppm for 1,1-DCE and 10 ppm for 1,2-DCE. The residual concentrations after 8 hours from the start of the experiment are shown in Table 4.

TABLE 4

|  | 1,1-DCE | Cis 1,2-DCE | Trans 1,2-DCE |
|---|---|---|---|
| Blank | 4.4 | 9.1 | 9.0 |
| Blank with 90% acidic water | 4.1 | 9.1 | 9.1 |
| Control | 1.6 | 3.9 | 4.6 |
| 60% acidic water | 0.5 | 2.0 | 2.6 |
| 70% acidic water | 0.4 | 2.0 | 2.6 |
| 80% acidic water | 0.4 | 1.8 | 2.3 |
| 90% acidic water | 0.4 | 1.7 | 2.2 |
|  |  |  | (ppm) |

The blanks containing 0% and 90% acidic water showed virtually no difference in DCE concentration, indicating the absence of DCE decomposition by the acidic water itself. The systems containing strain JM1 and acidic water more than 60% showed markedly accelerated DCE decomposition compared with the controls.

Example 13

Effect of Alkaline Water on DCE Decomposition by Strain JM1

An experiment was carried out in the same manner as in Example 11 except that 1,1-DCE (1,1-dichloroethylene), cis 1,2-DCE (cis 1,2-dichloroethylene), and trans 1,2-DCE (trans 1,2-dichloroethane) were used as the substances to be decomposed. These substances were added as a gas in air as with TCE and the initial concentrations were 5 ppm for 1,1-DCE and 10 ppm for 1,2-DCE. The residual concentrations after 8 hours from the start of the experiment are shown in Table 5.

TABLE 5

|  | 1,1-DCE | Cis 1,2-DCE | Trans 1,2-DCE |
|---|---|---|---|
| Blank | 4.6 | 9.4 | 9.4 |
| Blank with 90%. alkaline water | 4.3 | 9.3 | 9.4 |
| Control | 1.8 | 4.1 | 4.7 |
| 60% alkaline water | 0.3 | 1.9 |  |
| 70% alkaline water | 0.3 | 1.8 | 2.2 |

TABLE 5-continued

|  | 1,1-DCE | Cis 1,2-DCE | Trans 1,2-DCE |
|---|---|---|---|
| 80% alkaline water | 0.3 | 1.7 | 2.2 |
| 90% alkaline water | 0.3 | 1.7 | 2.2 |
|  |  |  | (ppm) |

The blanks containing 0% and 90% alkaline water showed virtually no difference in DCE concentration, indicating the absence of DCE decomposition by the alkaline water itself. The systems containing strain JM1 and alkaline water more than 60% showed markedly accelerated DCE decomposition compared with the controls.

Example 14

Effect of Electrolyzed Water on Aromatic Compound Decomposition by Strain JM1

An experiments were carried out in the same manner as in Examples 9 and 11 except that phenol, o-cresol, m-cresol, and toluene were used as the substances to be decomposed instead of TCE. The concentrations of the acidic water and the alkaline water were fixed at 80% and 5% for control. Strain JM1 was added to all systems other than blanks. Phenol and the cresol were added directly and toluene was added as a gas-in-air. The initial concentrations were 400 ppm for phenol, 300 ppm for cresol, and 200 ppm for toluene. The assay of phenol was performed by absorptiometry [Japanese Industrial Standard (JIS) K0102-1993 28.1] using 4-amino antipyrine, cresol by absorptiometry (JIS K0102-1993 28.2) using p-hydrazinobenzene sulfonic acid, and toluene by gas chromatography with an FID detector (a product of Shimadzu Seisakusho Ltd. GC-14B). The residual concentrations after 8 hours from the start of incubation are shown in Table 6.

TABLE

|  | Phenol | o-Cresol | m-Cresol | Toluene |
|---|---|---|---|---|
| Blank | 394 | 299 | 294 | 190 |
| Blank with 90% acidic water | 395 | 297 | 294 | 189 |
| Blank with 90% alkaline water | 391 | 297 | 293 | 189 |
| Control | 91 | 73 | 77 | 55 |
| 90% Acidic water | 40 | 21 | 21 | 16 |
| 90% Alkaline water | 33 | 20 | 18 | 12 |
|  |  |  |  | (ppm) |

The blanks containing 0% and 90% acidic or alkaline water showed virtually no difference in each aromatic compound concentration, indicating the absence of decomposition by the acidic or alkaline water itself. The systems containing strain JM1 and 90% acidic or alkaline water showed markedly accelerated aromatic compound decomposition compared with the controls.

Example 15

Effect of Electrolyzed Water on Decomposition of TCE in Polluted Soil by Strain JM1

One gram of the brown forest soil collected at Morinosato, Atsugi-shi, Kanagawa-ken was placed severally in 27 ml vials. Each vial was tightly sealed with a butyl rubber stopper and an aluminum cap, and 3 ml of a TCE-containing air prepared as in Example 8 was injected therein using a syringe. The vials were left standing at 15° C. for three days, and then 10 ml of solutions as prepared in Example 14 were added to vials severally, and TCE concentrations were periodically determined at 23° C. The residual concentrations after 8 hours from the start of incubation are shown in Table 7.

TABLE 7

|  | TCE |
|---|---|
| Blank | 41 |
| Blank with 90% acidic water | 37 |
| Blank with 90% alkaline water | 39 |
| Control | 14 |
| 90% Acidic water | 7 |
| 90% Alkaline water | 5 |
|  | (ppm) |

The blanks containing 0% and 90% acidic or alkaline water showed virtually no difference in TCE concentration, indicating the absence of TCE decomposition by the acidic or alkaline water itself. The systems containing strain JM1 and acidic or alkaline water more than 60% showed markedly accelerated TCE decomposition compared with the controls.

Example 16

Effect of Electrolyzed Water on Decomposition of TCE in Gaseous Phase Through Aeration of Culture of Strain JM1

Liquid cultures of strain JM1 were prepared as in Example 14 and 10 ml of each was placed in a vial, and then swept for three minutes at 60 ml/min with the air which had aerated a saturated aqueous TCE solution. The vials were tightly sealed with a butyl rubber stopper and an aluminum cap, and incubated at 25° C. to determine TCE concentrations periodically. The residual concentrations after 8 hours from the start of incubation are shown in Table 8.

TABLE 8

|  | TCE |
|---|---|
| Blank | 202 |
| Blank with 90% acidic water | 199 |
| Blank with 90% alkaline water | 196 |
| Control | 62 |
| 90% Acidic water | 39 |
| 90% Alkaline water | 35 |
|  | (ppm) |

The blanks containing 0% and 90% acidic or alkaline water showed virtually no difference in TCE concentration, indicating the absence of TCE decomposition by the acidic or alkaline water itself. The systems containing strain JM1 and acidic or alkaline water showed markedly accelerated TCE decomposition in the air compared with the controls.

Example 17

Effect of Acidic Water on Decomposition of TCE in Aqueous System by Strain JM1 at 4° C.

A colony of strain JM1 grown on an agar culture medium was transferred into 200 ml M9 medium containing 2.0% of sodium malate in a shaking culture flask, and subjected to shaking culture at 15° C. for 70 hours. Then 0.1 ml aliquots of the culture were inoculated in four sterile 50 ml tubes containing 10 ml of (0.22μ filter-sterilized) followings respectively: A) 2% sodium malate-containing M9 medium prepared with water (control), B) 2% sodium malate-containing M9 medium prepared with 60% acidic water, C) 2% sodium malate-containing M9 medium prepared with 75% acidic water, and D) 2% sodium malate-containing M9 medium prepared with 90% acidic water. After 10 days' culture, each culture was transferred to a 27 ml vial and tightly sealed therein with a butyl rubber stopper and an aluminum cap. Then TCE-containing air (air collected from a 27 ml vial containing 0.5 ml of neat TCE and left standing at 25° C. for one hour) was injected with a syringe to an initial concentration of 50 ppm (assuming that all TCE had completely dissolved in the culture fluid). Vials were continuously shaken at 4° C. and the TCE concentration in the gaseous phase of the vial was determine periodically by gas chromatography with an FID detector GC-14B (a product of Shimadzu Seisakusho Ltd.). Blank system contained 90% acidic water and no strain JM1. The TCE concentrations of the systems after three days' shaking are shown in Table 9.

TABLE 9

|  | A |  |  |  |
|---|---|---|---|---|
| (blank) | (control) | B | C | D |
| TCE concentration (ppm) 47.9 | 44.6 | 6.2 | 3.1 | 1.9 |

The blanks containing 90% acidic water showed virtually no decrease of TCE concentration, indicating the absence of TCE decomposition by the acidic water itself. The systems containing strain JM1 and acidic water not less than 60% showed markedly accelerated TCE decomposition compared with the controls. These results indicate that the culture systems using an acidic water are highly effective in decomposing TCE at a temperature as low as 4° C.

Example 18

Effect of Alkaline Water on Decomposition of TCE in Aqueous System by Strain JM1, at 4° C.

A colony of strain JM1 grown on an agar culture medium was transferred into 200 ml M9 medium containing 2.0% of sodium malate in a shaking culture flask, and subjected to shaking culture at 15° C. for 70 hours. Then 0.1 ml aliquot of the culture was inoculated in each of four sterile 50 ml tubes containing 10 ml of (0.22μ filter-sterilized) followings respectively: A) 2% sodium malate-containing M9 medium prepared with water (control), B) 2% sodium malate-containing M9 medium prepared with 60% alkaline water, C) 2% sodium malate-containing M9 medium prepared with 75% alkaline water, and D) 2% sodium malate-containing M9 medium prepared with 90% alkaline water. After the 10 days' culture, each culture was transferred into a 27 ml vial and tightly sealed with a butyl rubber stopper and an aluminum cap. Then TCE-containing air (air collected from a 27 ml vial containing 0.5 ml of neat TCE and left standing at 25° C. for one hour) was injected with a syringe to an initial concentration of 50 ppm (assuming that all TCE had completely dissolved in the culture fluid). Vials were continuously shaken at 4° C. and the TCE concentration in the gaseous phase of the vial was determine periodically by gas chromatography with an FID detector GC-14B (a product of Shimadzu Seisakusho Ltd.). Blank system contained 90% alkaline water and no strain JM1. The TCE concentrations after three days' shaking are shown in Table 10.

TABLE 10

|  | A |  |  |  |
|---|---|---|---|---|
| (blank) | (control) | B | C | D |
| TCE concentration (ppm) 48.2 | 44.5 | 7.6 | 4.3 | 2.8 |

The blanks containing 90% alkaline water showed virtually no decrease of TCE concentration, indicating the absence of TCE decomposition by the alkaline water itself. The systems containing strain JM1 and alkaline water not less than 60% showed markedly accelerated TCE decomposition compared with the controls. These results indicate that the culture systems using alkaline water are highly effective in decomposing TCE at a temperature as low as 4° C.

Example 19

Effect of Mixed Water on Decomposition of TCE in Aqueous System by Strain JM1, at 4° C.

A colony of strain JM1 grown on an agar culture medium was transferred into 200 ml M9 medium containing 2.0% of sodium malate in a shaking culture flask, and subjected to shaking culture at 15° C. for 70 hours. Then 0.1 ml aliquot of the culture was inoculated in each of four sterile 50 ml tubes containing 10 ml of (0.22μ filter-sterilized) followings respectively: A) 2% sodium malate-containing M9 medium prepared with water (control), B) 2% sodium malate-containing M9 medium prepared-with 60% mixed water, C) 2% sodium malate-containing M9 medium prepared with 75% mixed water, and D) 2% sodium malate-containing M9 medium prepared with 90% mixed water. The mixed water used in the present example was produced by mixing acidic water and alkaline water prepared in Example 1 in equal amounts. After the culture was continued for 10 days, each culture was transferred into a 27 ml vial and tightly sealed therein with a butyl rubber stopper and an aluminum cap. Then TCE-containing air (air collected from a 27 ml vial containing 0.5 ml of neat TCE and left standing at 25° C. for one hour) was injected with a syringe to an initial concentration of 50 ppm (assuming that all TCE had completely dissolved in the culture fluid). Vials were continuously shaken at 4° C. and the TCE concentration in the gaseous phase of the vial was determine periodically by gas chromatography with an FID detector GC-14B (a product of Shimadzu Seisakusho Ltd.). Blank system contained 90% mixed water and no strain JM1.

The TCE concentrations of the systems after three days' shaking are shown in Table 11.

TABLE 11

|  | A |  |  |  |
|---|---|---|---|---|
| (blank) | (control) | B | C | D |
| TCE concentration (ppm) 48.0 | 44.7 | 8.0 | 4.6 | 2.9 |

The blank containing 90% mixed water showed virtually no decrease of TCE concentration, indicating the absence of TCE decomposition by the mixed water itself. The systems containing strain JM1 and mixed water not less than 60% showed markedly accelerated TCE decomposition compared with the controls. These results indicate that the culture systems using a mixed water are highly effective in decomposing TCE at a temperature as low as 4° C.

Example 20

Effect of Electrolyzed Water on Decomposition of TCE in Aqueous System by Strain JM2N at 4° C.

A colony of strain JM2N grown on an agar culture medium was transferred into 200 ml M9 medium containing 2.0% of sodium malate in a shaking culture flask, and subjected to shaking culture at 15° C. for 70 hours. Then 0.1 ml aliquot of the culture was inoculated in each of four sterile 50 ml tubes containing 10 ml of (0.22µ filter-sterilized) followings respectively: A) 2% sodium malate-containing M9 medium prepared with water (control), B) 2% sodium malate-containing M9 medium prepared with 90% acidic water, C) 2% sodium malate-containing M9 medium prepared with 90% alkaline water, and D) 2% sodium malate-containing M9 medium prepared with 90% mixed water. After 10 days' culture, each culture was transferred into a 27 ml vial and tightly sealed therein with a butyl rubber stopper and an aluminum cap. Then TCE-containing air (air collected from a 27 ml vial containing 0.5 ml of neat TCE and left standing at 25° C. for one hour) was injected with a syringe to an initial concentration of 50 ppm (assuming that all TCE had completely dissolved in the culture fluid). These vials were continuously shaken at 4° C. and the TCE concentration in the gaseous phase of the vial was determine periodically by gas chromatography with an FID detector GC-14B (a product of Shimadzu Seisakusho Ltd.). Blank system is A contained no strain JM1. The TCE concentrations of the systems after three days' shaking are shown in Table 12.

TABLE 12

|  | Control (blank) | A (control) | B | C | D |
|---|---|---|---|---|---|
| TCE concentration (ppm) | 48.2 | 45.7 | 2.4 | 3.0 | 3.2 |

The results indicate that in the every culture systems containing strain JM2N and electrolyzed water clearly promoted decomposition of TCE as compared with the control and that the culture systems using the electrolyzed water were highly effective for strain JM2N in decomposing TCE at a temperature as low as 4° C.

Example 21

Effect of Electrolyzed Water on Decomposition of Aromatic Compound in Aqueous System by Strain J1 at 4° C.

A colony of strain J1 grown on an agar culture medium was transferred into 200 ml M9 medium containing 0.2% of yeast extract in a shaking culture flask, and subjected to shaking culture at 25° C. for 24 hours. Then 0.1 ml aliquot of the culture was inoculated in each of four sterile 50 ml tubes containing 10 ml of (0.22µ filter-sterilized) followings: A) 0.2% yeast extract-containing M9 medium prepared with water (control), B) 0.2% yeast extract-containing M9 medium prepared with 90% acidic water, C) 0.2% yeast extract-containing M9 medium prepared with 90% alkaline water, and D) 0.2% yeast extract-containing M9 medium prepared with 90% mixed water, respectively. After 10 days' culture at 4° C., each culture was transferred into a 27 ml vial, and into the vials, phenol, o-cresol, m-cresol, and toluene were added to a concentration of 200 ppm severally. Phenol, o-cresol, and m-cresol were added as aqueous solutions and each vials was tightly sealed with a butyl rubber stopper and an aluminum cap. Toluene was injected as a gas to the already tightly sealed vials in the same manner as with TCE using a syringe. Vials were continuously shaken at 4° C. and the concentrations of these compounds were determined periodically. The assay of phenol was performed by absorptiometry [Japanese Industrial Standard (JIS) K0102-1993 28.1] using 4-amino antipyrine, cresol by absorptiometry (JIS K0102-1993 28.2) using p-hydrazinobenzene sulfonic acid, and TCE concentration was determined by gas chromatography with an FID detector GC-14B (a product of Shimadzu Seisakusho Ltd.). Blank system was A containing no strain J1. The residual concentrations of the systems after three days' shaking are shown in Table 13.

TABLE 13

|  | Phenol | o-Cresol | m-Cresol | Toluene |
|---|---|---|---|---|
| blank | 199 | 198 | 198 | 192 |
| A (control) | 120 | 117 | 115 | 109 |
| B | 22 | 16 | 20 | 13 |
| C | 25 | 22 | 23 | 19 |
| D | 25 | 22 | 25 | 19 |

(ppm)

The result clearly shows that in the culture systems of strain J1, the electrolyzed water clearly promoted the decomposition of the aromatic compounds as compared with the control. It also shows that a culture system using the electrolyzed water is highly effective in decomposing aromatic compounds at a temperature as low as 4° C.

Example 22

Effect of Electrolyzed Water on Decomposition of DEC in Aqueous System by Strain JM1 at 4° C.

A colony of strain JM1 grown on an agar culture medium was transferred into 200 ml M9 medium containing 2.0% of sodium malate in a shaking culture flask, and subjected to shaking culture at 15° C. for 70 hours. Then, 0.1 ml aliquots of the culture were inoculated into sterile 50 ml tubes severally containing 0.22µ filter-sterilized 10 ml of A) 2% sodium malate-containing M9 medium prepared with water (control), B) 2% sodium malate-containing M9 medium prepared with 90% acidic water, C) 2% sodium malate-containing M9 medium prepared with 90% acidic water, and D) 2% sodium malate-containing M9 medium prepared with 90% mixed water, in triplicate. After the culture was continued for 10 days, each tube content was transferred into a 27 ml vial and each vial was tightly sealed with a butyl rubber stopper and an aluminum cap. To each set of tubes A–D, gaseous 1,1-dichloroethylene (1,1-DCE), cis 1,2-dichloroethylene (cis 1, 2-DCE), or trans 1,2-dichloroethylene (trans 1, 2-DCE) was injected with a syringe as with TCE to a concentration of 15 ppm (assuming complete dissolution of DCE into the culture). The vials were continuously shaken at 4° C. and the DCE concentrations in the gaseous phase in the vials were determine periodically by gas chromatography with an FID detector GC-14B (a product of Shimadzu Seisakusho Ltd.). Blank system was A containing no strain JM1. The DCE concentrations of the systems after three days' shaking are shown in Table 14.

TABLE 14

|   | 1,1-DCE | Cis 1,2-DCE | Trans 1,2-DCE |
|---|---|---|---|
| blank | 14.1 | 14.3 | 14.1 |
| A (control) | 13.0 | 12.8 | 12.6 |
| B | 4.1 | 2.3 | 2.1 |
| C | 4.6 | 2.6 | 2.6 |
| D | 4.7 | 2.9 | 2.7 |

(ppm)

The result shows that in the culture systems of strain JM1, the electrolyzed water promoted the decomposition of DCE as compared with the control. It also shows that a culture system using the electrolyzed water is highly effective in decomposing DCE at a temperature as low as 4° C.

Example 23

Effect of Electrolyzed Water on Decomposition of TCE in Polluted Soil by Strain JM1

One gram of the brown forest soil collected at Morinosato, Atsugi-shi, Kanagawa-ken was placed in each of 27 ml vials. Each vial was tightly sealed with a butyl rubber stopper and an aluminum cap and, 3 ml of a TCE-containing air prepared as in Example 8 was injected therein using a syringe, and then left standing at 4° C. for three days. Separately, a colony of strain JM1 grown on an agar culture medium was transferred into 200 ml M9 medium containing 2.0% of sodium malate in a shaking culture flask, and subjected to shaking culture at 15° C. for 70 hours. Then, 0.1 ml aliquots of the culture were inoculated into 4 of sterile 50 ml tubes containing (0.22$\mu$ filter-sterilized) 10 ml of A) 2% sodium malate-containing M9 medium prepared with water (control), B) 2% sodium malate-containing M9 medium prepared with 90% acidic water, C) 2% sodium malate-containing M9 medium prepared with 90% acidic water, or D) 2% sodium malate-containing M9 medium prepared with 90% mixed water respectively, and cultured at 4° C. for 10 days. Then these cultures (10 ml) were added to the above vials respectively, and left standing at 4° C. to determine TCE concentrations. The blank is A containing no strain JM1. The TCE concentrations after three days' standing are shown in Table 15.

TABLE 15

|   | TCE |
|---|---|
| Blank | 42.2 |
| A (Control) | 34.6 |
| B | 9.1 |
| C | 11.0 |
| D | 12.1 |

(ppm)

The result clearly shows that in the culture systems of strain JM1, the electrolyzed water promoted the decomposition of TCE in soil as compared with the control. It also shows that a culture system using the electrolyzed water is highly effective in purification of TCE-contaminated soil at a temperature as low as 4° C.

Example 24

Effect of Electrolyzed Water on Decomposition of TCE in Gaseous Phase by Aerating Strain JM2N Liquid Culture The four kinds of liquid cultures of JM2N were prepared as in Example 20, and 10 ml of each was placed in a vial, and then swept for three minutes at 60 ml/min with air which had aerated a saturated aqueous TCE solution. The vials were tightly sealed with a butyl rubber stopper and an aluminum cap, and incubated at 4° C. to determine TCE concentrations periodically.

Blank was A not containing strain JM2N. The TCE concentrations after 3 days' standing are shown in Table 16.

TABLE 16

|   | TCE |
|---|---|
| Blank | 192 |
| A (Control) | 172 |
| B | 49 |
| C | 53 |
| D | 58 |

(ppm)

The result clearly shows that in the culture systems of strain JM2N, the electrolyzed water promoted the decomposition of TCE in the gaseous phase as compared with the control. It also shows that a culture system using the electrolyzed water is highly effective in the purification of TCE-contaminated air at a temperature as low as 4° C.

Example 25

Effect of Electrolyzed Water on Decomposition of TCE in Aqueous System by Strain JM1 in the Presence of Butanol A colony of strain JM1 grown on an agar culture medium was transferred into 200 ml M9 medium containing 2.0% of sodium malate in a shaking culture flask, and subjected to shaking culture at 15° C. for 70 hours. Then, 0.1 ml aliquots of the culture were inoculated into 4 of 27 ml vials respectively containing 0.22$\mu$ filter-sterilized 10 ml of A) 2% sodium malate-containing M9 medium prepared with water (control), B) 2% sodium malate-containing M9 medium prepared with 90% acidic water, C) 2% sodium malate-containing M9 medium prepared with 90% acidic water, and D) 2% sodium malate-containing M9 medium prepared with 90% mixed water. To each vial, 1-butanol was added to 1% (v/v). Then each vial was tightly sealed with a butyl rubber stopper and an aluminum cap. Then TCE-containing air (air collected from a 27 ml vial containing 0.5 ml of neat TCE and left standing at 25° C. for one hour) was injected with a syringe to an initial concentration of 50 ppm (assuming that all TCE had completely dissolved in the culture fluid). Culture was carried out at 23° C. TCE concentration was determined by gas chromatography using an FID detector GC-14B, a product of Shimadzu Seisakusho. The results are shown in Table 17. Blank was A not containing JM1.

TABLE 17

|   | Control (blank) | A (control) | B | C | D |
|---|---|---|---|---|---|
| TCE (ppm) | 48.2 | 47.7 | 10.6 | 15.2 | 15.9 |

The result clearly shows that in the culture systems of strain JM1, the electrolyzed water promoted the decomposition of TCE as compared with the control. It also shows that a culture system using the electrolyzed water is highly effective in the decomposition treatment of TCE under such difficult conditions as the presence of 1.0% butanol.

What is claimed is:

1. A method for culturing a microorganism and promoting microbial growth and metabolism comprising the steps of:
   providing a microorganism; and
   culturing said microorganism in a culture medium, wherein the culture medium contains:
   (a) a carbon source being metabolizable by said microorganism, and
   (b) an electrolyzed water containing not more than 0.4 ppm chlorine formed by electrolyzing water containing an electrolyte in an electrolytic cell.

2. A method according to claim 1, wherein said electrolyzed water comprises an acidic water.

3. A method according to claim 2, wherein said acidic water has a pH value of 1–4 and a redox potential of 800 mV–1500 mV.

4. A method according to claim 2, wherein said acidic water has a pH value of 1–3 and a redox potential of not less than 800 mV.

5. A method according to claim 2, wherein said acidic water has a pH value of 1–2 and a redox potential of not less than 1100 mV.

6. A method according to claim 3, wherein said chlorine concentration is not more than 0.3 ppm.

7. A method according to claim 1, wherein said electrolyzed water contains an alkaline water.

8. A method according to claim 7, wherein said alkaline water has a pH value of 10–13 and a redox potential of −1000 mV–800 mV, said redox potential being determined by the use of a platinum electrode as a working electrode and a silver—silver chloride electrode as a reference electrode.

9. A method according to claim 7, wherein said alkaline water has a pH value of not less than 10.5 and a redox potential of not more than −600 mV.

10. A method according to claim 7, wherein said alkaline water has pH value of not less than 11 and a redox potential of not more than −800 mV.

11. A method according to claim 1, wherein said electrolyzed water comprises an acidic water and an alkaline water.

12. A method according to claim 1, wherein said microorganism exists in the natural world.

13. A method according to claim 12, wherein said microorganism is *Escherichia coli*.

14. A method according to claim 12, wherein said microorganism is strain J1 (FERM BP-5102).

15. A method according to claim 1, wherein said microorganism is a mutant strain.

16. A method according to claim 15, wherein said microorganism is strain JM1 (FERM BP-5352).

17. A method according to claim 15, wherein said microorganism is strain JM2N (FERM BP-5961).

18. A method according to claim 1, wherein said microorganism is an artificial recombinant.

19. A method according to any one of claims 12, 15 and 18, wherein said microorganism can decompose a pollutant.

20. A method according to claim 19, wherein said pollutant is an aromatic compound.

21. A method according to claim 20, wherein said aromatic compound is at least one member selected from the group consisting of phenol, toluene, and cresol.

22. A method according to claim 19, wherein said pollutant is a volatile organic halogenated compound.

23. A method according to claim 22, wherein said volatile organic halogenated compound is a halogenated aliphatic hydrocarbon compound.

24. A method according to claim 23, wherein said halogenated aliphatic hydrocarbon compound is at least one member selected from the group consisting of trichloroethylene and dichloroethylene.

25. A method for culturing a microorganism and promoting microbial growth and metabolism comprising the steps of:
   providing a microorganism; and
   culturing said microorganism in a culture medium, wherein the culture medium contains:
   (a) a carbon source being metabolizable by said microorganism, and
   (b) an acidic water having a pH value of 1–4 and a redox potential from 800 mV to 1500 mV previously obtained by electrolysis of water in an electrolytic cell.

26. A method according to claim 25, wherein said acidic water has a pH value of 1–3.

27. A method according to claim 25, wherein said acidic water has a pH value of 1–2.8 and a redox potential from 1100 mV to 1500 mV.

28. A method according to claim 25, wherein said acidic water has a chlorine concentration of not more than 0.4 ppm.

29. A method according to claim 28, wherein said chlorine concentration is not more than 0.3 ppm.

30. A method for culturing a microorganism and promoting microbial growth and metabolism comprising the steps of:
   providing a microorganism; and
   culturing said microorganism in a culture medium, wherein the culture medium contains:
   (a) a carbon source being metabolizable by said microorganism, and
   (b) an alkaline water having a pH value of 10–13 and a redox potential from −1000 mV to 800 mV previously obtained by electrolysis of water in an electrolytic cell, said redox potential being determined by the use of a platinum electrode as a working electrode and a silver—silver chloride electrode as a reference electrode.

31. A method according to claim 30, wherein said alkaline water has a pH value of 10.5–13 and a redox potential of −600 mV to −1000 mV.

32. A method according to claim 31, wherein said alkaline water has a pH value of 11–13 and a redox potential of −1000 mV to −800 mV.

* * * * *

UNITED STATES PATENT AND TRADEMARK OFFICE
CERTIFICATE OF CORRECTION

PATENT NO.      : 6,660,516 B1
DATED           : December 9, 2003
INVENTOR(S)     : Imamura et al.

It is certified that error appears in the above-identified patent and that said Letters Patent is hereby corrected as shown below:

<u>Title page,</u>
Item [56], References Cited, U.S. PATENT DOCUMENTS, insert:

| | | | |
|---|---|---|---|
| -- 4,761,208 | 8/1988 | Gram et al. | 204/95 |
| 5,108,563 | 4/1992 | Cook | 204/149 |
| 5,681,739 | 10/1997 | Turick et al. | 435/262.5 |
| 5,731,008 | 3/1998 | Morrow | 424/613 |
| 5,840,191 | 11/1998 | Eccles | 210/601 |
| 5,846,397 | 12/1998 | Manzatu et al. | 205/748 |
| 5,902,744 | 5/1999 | Gray et al. | 435/262.5 |
| 5,945,331 | 8/1999 | Kozaki et al. | 435/262 --. |

OTHER PUBLICATIONS, "Database WPI (second occurrence) reference, "Secrtion" should read -- Section --.

<u>Column 2,</u>
Line 10, "*Pseudombnas putida*" should read -- *Pseudomonas putida* --.

<u>Column 8,</u>
Line 47, "an aerobic" should read -- aerobic --.

<u>Column 9,</u>
Line 10, "JM1," should read -- JM1 --.

<u>Column 11,</u>
Line 19, "the,production" should read -- the production --.
Line 30, "reduce" should read -- reduces --.

<u>Column 12,</u>
Line 13, "those express" should read -- is those expressing --, and "(express" should read -- (expressing --.

<u>Column 13,</u>
Line 12, "into contact" should read -- to come into contact --.
Line 17, "Here" should read -- Here, --.

<u>Column 15,</u>
Line 26, "were, a bacterial strain (strain" should read -- were bacterial strain --.
Line 30, "(FERM BP-5961" should read -- (FERM BP-5961) --.

<u>Column 18,</u>
Line 8, "(OD),was" should read -- (OD) was --.

UNITED STATES PATENT AND TRADEMARK OFFICE
CERTIFICATE OF CORRECTION

PATENT NO.     : 6,660,516 B1
DATED          : December 9, 2003
INVENTOR(S)    : Imamura et al.

It is certified that error appears in the above-identified patent and that said Letters Patent is hereby corrected as shown below:

Column 20,
Line 6, "water:" should read -- water --.
Line 65, (Table 5), "0.3    1.9" should read -- 0.3    1.9    2.3 --.

Column 21,
Line 21, "experiments were" should read -- experiment was --.

Column 23,
Lines 17 and 63, "determine" should read -- determined --.

Column 24,
Line 45, "determine" should read -- determined --.

Column 25,
Line 26, "determine" should read -- determined --.
Line 39, "the every culture systems" should read -- every culture system --.
Line 67, "vials" should read -- vial --.

Column 26,
Line 61, "determine" should read -- determined --.

Column 29,
Line 36, "has PH" should read -- has a pH --.

Signed and Sealed this

Twenty-eighth Day of March, 2006

JON W. DUDAS
*Director of the United States Patent and Trademark Office*